United States Patent [19]

Jack et al.

[11] Patent Number: 5,716,610
[45] Date of Patent: *Feb. 10, 1998

[54] METHOD AND COMPOSITION FOR TOPICAL TREATMENT OF DAMAGED TISSUE USING HISTAMINE PHOSPHATE AS ACTIVE INGREDIENT

[75] Inventors: Bruce A. Jack; B. Thomas White, both of Albuquerque, N. Mex.

[73] Assignee: Professional Pharmaceutical, Inc., Albuquerque, N. Mex.

[*] Notice: The term of this patent shall not extend beyond the expiration date of Pat. No. 5,294,440.

[21] Appl. No.: 691,446

[22] Filed: Aug. 2, 1996

Related U.S. Application Data

[63] Continuation of Ser. No. 199,103, Feb. 22, 1994, abandoned, which is a continuation-in-part of Ser. No. 886,304, May 21, 1992, Pat. No. 5,294,440, which is a continuation of Ser. No. 715,410, Jun. 14, 1991, abandoned.

[51] Int. Cl.$^6$ .............................. A61K 31/13; A61K 9/10
[52] U.S. Cl. ..................... 424/78.05; 424/78.24; 514/887; 514/937; 514/969; 514/400
[58] Field of Search ....................... 514/937, 969, 514/400, 887; 424/78.05, 78.24

[56] References Cited

U.S. PATENT DOCUMENTS

| | | | |
|---|---|---|---|
| 4,540,572 | 9/1985 | Seth | 424/81 |
| 4,618,490 | 10/1986 | De Marco | 424/80 |
| 4,966,892 | 10/1990 | McAnalley | 536/102 |

OTHER PUBLICATIONS

Inflammation and the Function of Leukocytes, A.C. Guyton, Textbook of Medical Physiology, pp. 72–73 and 86.

The Pharmacological Basis of Therapeutics, Louis S. Goodman and Alfred Gilman, Fifth Edition, pp. 595–600.

*Primary Examiner*—Raj Bawa
*Attorney, Agent, or Firm*—Cahill, Sutton & Thomas

[57] ABSTRACT

A pharmaceutical composition of water, water soluble vinyl polymer gel, amine alcohol dispersant and IEP is used topically to treat herpes labialis and aphthous stomatitis lesions, and also to treat herpes genitalis, chicken pox, allergic conjunctivitis, giant papillary conjunctivitis, stomatitis secondary to chemotherapy, thermal burn, sunburn, decubitus ulcers and shingles.

7 Claims, No Drawings

1

METHOD AND COMPOSITION FOR TOPICAL TREATMENT OF DAMAGED TISSUE USING HISTAMINE PHOSPHATE AS ACTIVE INGREDIENT

CROSS REFERENCE TO RELATED APPLICATIONS

This application is a continuation of patent application Ser. No. 08/199,103, filed Feb. 22, 1994, now abandoned, which is a continuation-in-part of commonly assigned allowed application Ser. No. 07/886,304, filed May 21, 1992 and which issued into U.S. Pat. No. 5,294,440 on Mar. 15, 1994, which is a continuation of commonly assigned application Ser. No. 07/715,410, filed Jun. 14, 1991, now abandoned.

BACKGROUND OF THE INVENTION

The invention relates to compositions and methods for the treatment of the viral diseases herpes labialis (cold sores or fever blisters), herpes genitalis, herpes zoster (shingles), varicella zoster (chickenpox); inflammatory diseases and/or diseases demonstrating compromise or reaction of the immune system including aphthous stomatitis (canker sores), oral mucositis (stomatitis) secondary to chemotherapy, allergic conjunctivitis, giant papillary conjunctivitis; and lesions of injury to the skin including photodermatitis (sunburn, specifically second degree sunburn), thermal burns and pressure sores (decubitus ulcers).

Histamine phosphate previously has been used as a diagnostic agent for determining a condition known as achlorhydria. Histamine phosphate also has been used intradermally to produce a flare-up reaction of the skin to test the ability of certain drugs to inhibit this histamine-induced wheal, thereby indicating clinical response for disease processes which liberate histamine.

The histamine phosphate referred to is the compound 1H-imidazole-4-ethanamine,phosphate (IEP), and is currently used in subcutaneous administration for the diagnosis of gastric function. Principle effects of IEP from subcutaneous, intramuscular or intravenous administration occur on the vascular system, smooth muscles, and exocrine glands. In humans, IEP produces vasodilation in the blood vessels and capillaries, causing a flushing of the face, reduction in systemic blood pressure, increase in skin temperature, and increased capillary permeability sufficient to produce exudation of fluid, plasma proteins, and erythrocytes into extracellular spaces.

Intracutaneous injection of 0.01–0.02 milligrams of IEP can create a characteristic "triple response" including a reddening at the site of injection, a wheal or patch of localized edema within 20–60 seconds, followed by a bright halo or flare around the wheal.

There is considerable species variation with regard to the response of smooth muscles to IEP. In humans, IEP stimulates smooth muscle contraction of the gastrointestinal (GI) tract, contraction of the sphincter of Oddi and bile duct, and potent bronchoconstriction in patients with bronchial asthma, emphysema, or bronchitis. IEP has little effect on the smooth muscle of the uterus and has little bronchoconstrictor effect on healthy individuals.

IEP is metabolized in the liver by methylation and oxidation, and the metabolites are excreted in the urine. IEP is largely inactive when given by mouth. No information has been found regarding the extent of systemic absorption following topical administration of IEP. It has been suggested by Kahlson, et. al., that tissue intrinsic histamine-forming capacity might play a beneficial role in the healing process of certain types of tissue damage.

The carbopol gel base is widely used in the cosmetic industry and has been proven safe.

Recurrent herpes simplex stomatitis may occur on the lips or intraorally. Outbreaks may be associated with trauma, fatigue, menstrual cycle, emotional upset, or exposure to sunlight. Vesicles, or intraepithelial blisters, usually are preceded by burning, swelling and soreness in the area where lesions subsequently develop. Vesicles are small, 1 millimeter in diameter or less and may coalesce to form larger lesions. These vesicles rupture quickly leaving small ulcerations. The most common sites of recurrent intraoral lesions are the hard palate and attached gingiva. Lesions gradually heal within 7–10 days producing no scarring.

Due to the widespread practice of oral sex, it appears that either herpes simplex 1 and/or herpes simplex 2 lesions can occur orally or genitally. Genital herpetic lesions usually develop within 4–7 days after contact and may vary in nature from non-specific itching and soreness to erythema on the skin or mucous membranes to the development of painful vesicles which erode and form superficial, circular ulcers with a red areola. The ulcers become crusted in a few days and usually heal in about 10 days, with scarring. Recurrent genital herpetic disease may be quite frequent and may be prolonged over many years.

Herpes zoster (shingles) lesions are characterized by vesicular eruption and neuralgic pain in the cutaneous areas supplied by peripheral sensory nerves in the dorsal root ganglia affected by the virus. Herpes zoster is usually activated by local lesions involving the nerve containing the latent virus, systemic disease, particularly Hodgkin's disease, or by suppression or compromise of the immune system. Following a prodromal period of 3–4 days including symptoms of chills, fever, malaise and G.I. disturbances, characteristic crops of vesicles on an erythematous base appear in cutaneous areas innervated by the affected root ganglia. The involved area of the skin is usually hyperesthetic and the associated pain may be severe. Lesions usually begin to dry and scab within 10–14 days, but the outbreak of new clusters of vesicles can prolong the disease episode for weeks. Post herpetic neuralgia associated with herpes zoster may persist for months or years. Herpes zoster is caused by the varicella-zoster virus, the same virus that causes chickenpox with chickenpox being the acute, invasive phase of the virus and zoster (shingles) being the reactivation of the latent phase.

The usual incubation period for chickenpox following exposure to the virus is 10–14 days and the lesions erupt in successive crops for up to 6 days. Lesions progress from macule to papule to vesicle and usually begin crusting within 6–8 hours. Itching associated with the lesions may be severe and it is important to prevent scratching which may lead to widespread infection and disfigurement.

Aphthous stomatitis lesions (canker sores) are characterized by the development of painful, recurring necrotizing ulcerations of the oral mucosa either as solitary or multiple lesions. Etiology is unclear; however, considerable evidence suggests the disease may be an immunologic hypersensitivity response to an L-form streptococcus bacterium. Precipitating factors in canker sore lesions may include trauma (dental procedures), self-inflicted bites (as in eating), endocrine changes (premenstrual periods, following childbirth, menopause), acute psychological problems (period of increased stress), and allergic responses (asthma, eating certain foods or taking certain medications).

The aphthous ulcer can begin as a single or a multiple superficial erosion of the oral mucosal epithelium covered by a gray membrane. The most common sites of occurrence are the mucosa of the lips and cheeks, soft palate, tongue, pharynx, and all locations of unattached (to bone) gingiva and mucosa. The ulcers persist for 7–10 days and heal gradually producing no scarring.

Oral mucositis (stomatitis), a common side effect of chemotherapy, may develop when chemotherapeutic agents used to treat various neoplastic diseases interfere with the maturation and replication of the cells that comprise the oral epithelium. The condition may be focal or generalized and involve the buccal mucosa, palate, tongue, floor of the mouth and the gingiva. Oral mucositis is painful and as a result patients neglect oral hygiene and fail to maintain adequate nutrition and hydration. The compromised epithelial barrier can also facilitate invasion of potentially lethal bacteria and fungi that may lead to local infections and/or septicemia.

Photodermatitis or sunburn results from overexposure of the skin to ultraviolet rays of 280–320 nm. Symptoms appear in 1–24 hours and peak in 72 hours. Changes in the epithelium of the skin range from mild erythema (first degree burn) to pain, swelling, skin tenderness and blisters (second degree burn). Fever, chills, weakness, dehydration and shock can occur if the sunburn is sufficiently severe and/or occupies a large portion of the body surface area. Upon eruption of any blisters formed or exfoliation, the skin may be hypervulnerable to infection and sunlight for up to several weeks.

Tissue injury caused by thermal burns results in protein denaturation, burn wound edema and loss of intravascular fluid volume due to increased vascular permeability. The depth of the burn may be described as first, second or third degree. Pain or sensitivity to the touch is usually associated with first and second degree burns and blister formation is a common presentation of second degree burns. The severity of the burn is judged by quantity of tissue (body surface area) involved. Pain, increased susceptibility to infection, and scarring are the most common complications associated with thermal burns.

A pressure sore (decubitus ulcer) results when tissues overlying a bony prominence have been subjected to prolonged pressure resulting in ischemic necrosis and ulceration. Decubitus ulcers can affect not only superficial tissues, but can also involve muscle and bone and the recognized stages of decubitus ulcer formation (Stage 1 through Stage 6) correspond to the tissue layers involved and the degree of involvement. The decubitus ulcer lesion, when open at any stage, poses a risk of infection and, dependent upon the depth of the lesion and the proper elimination of the pressure, can lead to tissue necrosis, epidermal desquamation, osteitis and septicemia. Surgical intervention may be required for deep lesions or lesions in which healing by current therapies is unsuccessful.

Allergic conjunctivitis may occur as part of a larger allergic syndrome, such as hayfever, or may occur alone as a result of direct contact with airborne substances such as pollen, fungus spores, various dusts, or animal danders. Itching and excessive lacrimation are prominent symptoms of allergic conjunctivitis as is edema and hyperemia of the conjunctiva. Release of endogenous histamine from mast cells seems largely responsible for the results of the allergic response.

Giant papillary conjunctivitis is a specific conjunctival inflammatory reaction to the materials used in the fabrication of soft contact lenses. Although the condition is similar to allergic conjunctivitis, it is characterized by papillary hypertrophy and probably represents a chronic conjunctival inflammatory reaction to denatured proteins that become adherent to the anterior lens surface. Conjunctival changes progress and include itching, lens instability, mucoid discharge and contact lens intolerance. Again, the release of endogenous histamine from mast cells seems largely responsible for the results of the allergic response.

There are a number of over-the-counter medications for cold sores (fever blisters), canker sores, oral ulcerations and the like, including BLISTEX, ZILACTIN, and CAMPHO PHENIQUE. A prescription medication also is available, under the trademark ZOVIRAX. However, for many persons suffering from cold sores, fever blisters, etc., none of these medications is very effective. ZOVIRAX is effective when taken orally by interfering with the replication of the herpes virus at the genetic level. We are concerned that there is potential for adverse reactions any time a patient takes medication systemically that interferes with DNA replication because of the risk of the medication interfering with normal cell DNA replication within the body, as is known to occur as a result of chemotherapy agents which are targeted to interfere with genetic replication of cancer cells and sometimes produce long term adverse side effects.

There are no effective over-the-counter remedies or medications for the treatment of herpes genitalis, herpes zoster (shingles), varicella zoster (chickenpox), photodermatitis (sunburn), thermal burns, pressure sores (decubitus ulcers), allergic conjunctivitis or giant papillary conjunctivitis that alter the progression or severity of any of these disease states. Analgesics, humectants, topical anesthetics, and antihistamines might provide temporary symptomatic relief in any or all of the above disease states, but will generally not change the course or severity of the disease or its lesions. Prescription medications are available for some of these disease indications. However, the only one which has proven any effectiveness in treatment is, again, oral (systemic) ZOVIRAX which is used to treat herpes genitalis, herpes zoster and varicella zoster. Topical silver sulfadiazine 1% cream, also available by prescription, has been used to treat herpes zoster and pressure sores, but without definite double-blind clinical trials showing effectiveness to support this therapy. Prescription topical debriding agents are available for the removal of the necrotic tissue associated with pressure sores; however, once the necrotic tissue has been removed, these agents must be discontinued as they will retard healing of the ulcer. Topical ophthalmic solutions are available, mostly by prescription, which contain vasoconstricting agents or steroids and act only to temporarily relieve the symptoms associated with conjunctivitis.

There is an unmet need for an effective remedy for the viral diseases herpes labialis (cold sores or fever blisters), herpes genitalis, herpes zoster (shingles), varicella zoster (chickenpox); inflammatory diseases or diseases demonstrating compromise or reaction of the immune system such as aphthous stomatitis (canker sores), oral mucositis (stomatitis) secondary to chemotherapy, allergic conjunctivitis, giant papillary conjunctivitis; and lesions of injury to the skin such as photodermatitis (sunburn, specifically second degree sunburn), thermal burns and pressure sores (decubitus ulcers).

SUMMARY OF THE INVENTION

It is an object of the invention to provide improved medication and treatment for herpes labialis and aphthous stomatitis lesions, i.e., for fever blisters, cold sores and canker sores, and the like.

It is another object of the invention to provide a medication for treatment of herpes labialis and aphthous stomatitis lesions having the highest concentration possible without producing damaging local tissue responses.

It is another object of the invention to provide a medication of the type described that is odorless, tasteless, and leaves no residue when it dries.

It is another object of the invention to provide a composition for treatment of herpes labialis and aphthous stomatitis lesions which can stop progression of the lesion in any phase of its development.

It is another object of the invention to provide a composition and treatment for treatment of lesions induced by various herpes viruses.

It is another object of the invention to provide a composition and treatment for a wide variety of lesions caused by herpes viruses, allergic conjunctivitis and giant papillary conjunctivitis, stomatitis secondary to chemotherapy, second degree sunburn, third degree thermal burns, and aphthous stomatitis.

Briefly described and in accordance with one embodiment thereof, the invention provides a composition and method of use for topical treatment of epithelial lesions for various herpes-caused lesions and various other lesions and inflammations such as aphthous stomatitis, stomatitis secondary to chemotherapy, photodermatitis, thermal burns, and decubitus ulcers. The preparation includes a water soluble vinyl polymer gel base, such as CARBOPOL 940 mixed uniformly with water, a neutralizing and emulsifying agent, and an effective amount of histamine phosphate (IEP). The composition is comprised of a water soluble gel of the vinyl polymer type uniformly mixed with approximately 0.00325 to 0.0275 percent by weight 1H-imidazole-4-ethanamine, phosphate (IEP), and is prepared by adding vinyl polymer to distilled water, allowing the resulting mixture to stand until the vinyl polymer mixture is wetted, blending the mixture with a high speed blender until a homogenous mixture is formed, adding a dispersing agent to form an emulsion, adding 0.00325 percent to 0.0275 percent 1H-imidazole-4-ethanamine,phosphate (IEP) by weight to the emulsion and mixing it until the resulting mixture is homogenous. Another composition, for treatment of allergic conjunctivitis and giant papillary conjunctivitis, is composed of semisynthetic water soluble polymer ophthalmic solution uniformly combined with approximately 0.0067 percent by weight 1H-imidazole-4-ethanamine, phosphate (IEP).

DETAILED DESCRIPTION OF PREFERRED EMBODIMENTS OF THE INVENTION

In accordance with the present invention, new formulations and treatments have been discovered which, when applied topically to the viral diseases herpes labialis (cold sores or fever blisters), herpes genitalis, herpes zoster (shingles), varicella zoster (chickenpox); inflammatory diseases and or diseases demonstrating compromise or reaction of the immune system including aphthous stomatitis (canker sores), oral mucositis (stomatitis) secondary to chemotherapy, allergic conjunctivitis, giant papillary conjunctivitis; and lesions of injury to the skin including photodermatitis (sunburn, specifically second degree sunburn), thermal burns and pressure sores (decubitus ulcers), have been found to be very effective in either preventing lesions from occurring, minimizing the severity of lesions that are formed, or mitigating the duration and pain from such lesions already developed. Preliminary evaluation indicates that if the medication of the present invention is applied initially when symptoms of a lesion or inflammatory reaction are first developing (when numbness, prickling sensation, itching, etc. are experienced), subsequent phases of the lesion or inflammatory reaction do not develop or develop to a lesser degree than would otherwise be seen.

In all the following examples, unless otherwise noted, no persons under 18 years of age or pregnant or lactating females were admitted to the studies. All subjects were required to be free from abnormalities or diseases of the skin, mucous or conjunctival membranes (except the disease or medical entity studied), and free of allergies, asthma, emphysema, bronchitis, peptic ulcer disease, hiatal hernia or other intestinal disease. Randomized double blind procedures, in which subjects were assigned randomly to one or more active ingredient levels being evaluated by weight of active ingredient, were performed utilizing treatment labels stating "Concentration A", Concentration B", etc. to ensure "blindness" of the investigator as well as the patient. The protocol for the studies was reviewed by the Institutional Review Board at St Joseph Medical Center of Albuquerque in an attempt to ensure safety of the patients participating in the various studies performed and to verify control of all variables involved in the studies through careful standardization of care in each study so that the only difference between treatment groups was the active ingredient concentration. With such standardization of care and care in setting up each study, the differences between treatment groups due to the variation and/or the presence of active ingredient concentration was found to be either "significant" or "highly significant" or "not significant". With careful control of variables and strict standardization of care in all studies performed, statistically valid inferences could be made, even in small treatment groups.

EXAMPLE 1—HERPES LABIALIS AND APHTHOUS STOMATITIS

The composition of the present invention includes initial preparation of a gel base by adding 0.8% CARBOPOL 940, which is a vinyl polymer, to distilled water. This mixture was allowed to stand for several hours until the polymer was wetted and a gel was formed. This mixture then was blended by means of a ordinary high speed mixer, such as a Lightning Labmaster II until a homogenous mixture is formed. At this point, a neutralizing and emulsifying agent such as an amino alcohol was added, forming an emulsion. Then, IEP totaling 0.0067 percent by weight of the total formulation was added to the gel and blended until a homogenous composition was obtained. This composition then was applied topically to various types of lesions, as subsequently described.

(In all of the subsequent examples described herein, the above method is utilized to prepare the composition, except that IEP totalling the indicated percent by weight was utilized instead of the 0.0067 of the present example, and in Examples 11 and 12 in which an ophthalmic solution was utilized. In those examples, "MUROCELL" was utilized as the carrier for the specified percentage by weight of histamine phosphate. Generally, ophthalmic solutions that are commercially available include a 0.5 to 1.0 percent of semi-synthetic water soluble polymer plus purified water, boric acid, propylene glycol, sodium borate, sodium chloride, hydrochloric acid and/or sodium hydroxide to adjust the pH. Propylparaben or methylparaben may be used as a preservative. For "unidose" dispensers containing only two to three drops, no preservatives are used, as it is known that preservatives in ophthalmic solutions frequently cause undesirable side effects. The term semi-synthetic water soluble polymer as used herein includes hydroxy methylcellulose or carboxy methylcellulose. Carbopol is widely available in different viscosities. For example, Carbopol 934, Carbopol 938, Carbopol 940, Carbopol 941, etc. all have the same composition, but are of different viscosities.)

For Example 1 the above preparation was used by fifty to sixty patients exhibiting herpetic stomatitis lesions (fever blisters or cold sores) and three patients with aphthous ulcers (canker sores). Treatment consisting of topical application of the medication four to five times a day at the lesion site.

All patients experienced a decrease in healing time compared to an untreated episode. Table 1.1 shows the results for nine of the patients. Data was gathered from the other patients on a more informal basis, but all reported great improvement over the results of using other medications. Approximately two-thirds of the total patients in both treatment groups experienced the abortion of lesions, that is, when the medication was applied at the time of the first sensation of burning, tautness or swelling, no lesion developed.

Table 1.2 data show the reduction of clinical symptoms or signs for the same nine patients after one application and after one day of treatment, including the reduction in both size and spreading of lesions. All patients experienced a decrease in clinical symptoms and in the size of the lesions developed, beginning with the initial treatment.

TABLE 1.1

|  | DISEASE STATE | |
| --- | --- | --- |
|  | HERPES LABIALIS | APHTHOUS STOMATITIS |
| Percentage decrease in healing time compared to untreated episode | 49% | 67% |
| Percentage of patients who experienced lesion abortion | 60% | 67% |
| Estimated number of applications needed to eliminate clinical symptoms | 5 | 9 |

TABLE 1.2

|  | HERPES LABIALIS REDUCTION AFTER | | APHTHOUS STOMATITIS REDUCTION AFTER | |
| --- | --- | --- | --- | --- |
| CLINICAL SYMPTOM | 1 APP. | 1 DAY | 1 APP. | 1 DAY |
| Pain | 58% | 87% | 73% | 80% |
| Burning | 63% | 92% | 20% | 40% |
| Itching | 60% | 97% | None Reported | |
| Swelling | 27% | 72% | 20% | 50% |
| Size | 10% | 32% | 23% | 43% |
| Spreading | 40% | 62% | None Reported | |

EXAMPLE 2—HERPES LABIALIS—SECOND STUDY

The safety and effectiveness of IEP administered topically to cold sore (herpes labialis) lesions was evaluated in 18 patients. Subjects were placed in either of two groups: Group I subjects, who had no lesions at the initial visit, or Group II subjects who presented with lesions at time of enrollment in the study. Subjects in both groups were randomly assigned to use one of four IEP concentrations of 0.0%, 0.00083%, 0.0033% and 0.0067% by weight of active ingredient. There were no untoward reactions in any treatment group. Decrease in lesion size over time generally was more rapid with increasing active concentration. An analysis of variance of the placebo and 0.0067% treatment results showed the 0.0067% treatment to be significantly more effective ($p<0.05$) in reducing lesion size over time.

Prospective subjects were considered for the study only if they had experienced two or more episodes of herpes labialis lesions per year.

Subjects were assigned to either treatment Group I (no active lesion) or Group II (active lesion). Within groups, patients were assigned randomly to one of the four active ingredient levels being evaluated. This random assignment was made in groups of four patients to assure that each concentration was represented once in each group of four. Assignment of subjects within groups to the four concentrations was unknown to the investigator.

Subjects exhibiting no prodromal symptoms at time of enrollment (Group I) were provided product and instructions for application and instructions on recording onset of symptoms and time of applications of medication. Subjects entering the study with active lesions (Group II) were instructed to begin application immediately and to record size and duration of lesion(s) and times of application. Subjects in both groups were instructed to topically apply the product five times a day at the lesion site.

Subjective evaluation included an estimation of burning, pain, itching and swelling associated with lesions. Data sheets were provided on which a score of from 1 (none) to 5 (worst) could be scored by the subject. Clinical evaluation included daily classification of the phase or stage of lesions and size, number and location of lesions and subject compliance with the study regimen and use of other medication. Photographic records of lesion progression or degression were made for each subject at each visit.

Table 2.1 shows the number of subjects for each group participating in the study. No untoward events or significant complications associated with the use of any of the four test compositions were observed in this study.

TABLE 2.1

|  | # Patients entering study | # Patients completing study | # Patients active in study | # Patients withdrawn from study |
| --- | --- | --- | --- | --- |
| Group 1 | 19 | 3 | 13 | 3 |
| Group 2 | 20 | 15 | 0 | 5 |

Table 2.2 summarizes the percent effectiveness of each gel concentration in reducing lesion size as a function of time when compared to initial measurements taken on entrance to the study. Generally, it can be seen that as the quantity of active ingredient increased, the rate of lesion decrease was more rapid.

TABLE 2.2

| (Average % reduction in lesions from original size) | | | | |
| --- | --- | --- | --- | --- |
| % Gel Conc. | 24 Hours | 48 Hours | 72 Hours | 96 Hours |
| 0.0% | *[180.9] | *[196.4] | *[155.9] | *[157.0] |
| 0.00083% | *[14.0] | 14.0 | 27.6 | 44.3 |
| 0.0033% | 11.8 | 44.6 | 57.8 | 61.6 |
| 0.0067% | 37.5 | 67.0 | 86.2 | 98.9 |

*[ ] represent % growth rather than reduction

Subjective ratings of reduction in pain by the patients for pain, burning, itching, swelling and spreading are listed in Table 2.3. The values are shown for each active ingredient concentration and represent the average percent reduction of the original symptom. Based upon these data, it would appear that symptomologic relief was about the same for all concentrations tested, and that there was not a good correlation between symptomatic relief and physical diminishment of the lesions.

Reduction in lesion area (decay rate) over time as a function of concentration of active ingredient was calculated for subjects in each of the four treatment groups. Table 2.4 shows the number of subjects in each group and the number of lesions presented by each subject. The decay rate was calculated by first computing the percentage decrease in size of the lesion over time and then standardizing the decay rate over an exact 24 hour period. This standardization allowed a more meaningful statistical comparison of and subsequent inferences from decay rates across treatments. These decay rates are shown in Table 2.5 for each treatment group.

After calculating a standardized decay rate per lesion, an average decay rate for each subject was computed. Decay rates were computed for each lesion assessment and then averaged across assessments; for patients with multiple lesions, decay rates were averaged across lesions. Table 2.5 shows the mean percentage decay rates for 18 subjects across four treatment groups. Comparing the mean decay rates of the four treatment groups shown in Table 2.4 with the mean percentage decay rates for each subject, it appeared that treatment groups varied in lesion decay rates.

In order to determine if these observed differences were significant, a statistical analysis of the decay rates was performed. Subject decay rates were subjected to an analysis of variance (ANOVA) with treatment group as a between-subjects factor. The results of the omnibus test was $F(3,14)=4.60$. The critical F value for 3 and 14 degrees of freedom at the 0.05 significance level is 3.34. Thus, a significant overall treatment effect occurred as measured by lesion decay rates. Of particular interest was whether the placebo group was significantly different from the group receiving the highest level of active ingredient (0.0067%). A Scheffe follow-up test was performed to compare the means of these two groups. The result was $F(1,14)=13.06$. The critical F factor for the Scheffe test at the 0.05 significance level is 10.02. Hence, the two groups were significantly different.

The results of this study show that with increasing concentration of active ingredient, there generally was an increase in the decay rate of the lesions of subjects in the respective treatment groups. A statistical comparison of results between the placebo and highest level of active ingredient (0.0067%) showed that IEP was statistically significantly more effective ($p<0.05$) in reducing the size of lesions for herpes labialis patients.

TABLE 2.3

(Average percent reduction of original symptom)

|  | Day 1 | Day 2 | Day 3 | Day 4 | Day 5 | Day 6 |
|---|---|---|---|---|---|---|
| 0% |  |  |  |  |  |  |
| Pain | 25.0 | 83.4 | 100 | 91.7 | 91.7 | 100 |
| Burning | 50.0 | 66.7 | 88.9 | 77.8 | 77.8 | 100 |
| Itching | 58.3 | 56.3 | *[31.3] | 66.7 | 50.0 | 100 |
| Swelling | 4.2 | 35.3 | 40.0 | 69.2 | 60.0 | 100 |
| Spreading | 50.0 | 50.0 | 50.0 | 77.8 | 62.5 | 83.4 |

TABLE 2.3-continued (Average percent reduction of original symptom)

|  | Day 1 | Day 2 | Day 3 | Day 4 | Day 5 | Day 6 |
|---|---|---|---|---|---|---|
| 0.00083% |  |  |  |  |  |  |
| Pain | 34.2 | 51.7 | 51.7 | 65.0 | 64.4 | 66.7 |
| Burning | 20.9 | 66.7 | 58.3 | 75.0 | 77.8 | 66.7 |
| Itching | 41.7 | 47.8 | 16.7 | 11.1 | 41.7 | 75.0 |
| Swelling | 10.4 | 37.5 | *[8.3] | 75.0 | 55.6 | 0 |
| Spreading | 0 | 0 | 11.1 | 22.2 | 50.0 | 66.7 |
| 0.0033% |  |  |  |  |  |  |
| Pain | *[55.4] | *[19.2] | 33.3 | 66.8 | 66.7 | 83.4 |
| Burning | 21.7 | 37.5 | 62.5 | 68.8 | 100 | 87.5 |
| Itching | 23.4 | 55.0 | 58.5 | 75.0 | 82.5 | 100 |
| Swelling | *[308] | 45.4 | 55.8 | 55.9 | 65.0 | 66.7 |
| Spreading | 50.0 | 50.0 | 16.7 | 100 | 100 |  |
| 0.0067% |  |  |  |  |  |  |
| Pain | 66.7 | 83.4 | 55.6 | 55.6 | 100 | Not Scored |
| Burning | 50.0 | 100 | 100 | 100 | 100 | Not Scored |
| Itching | 50.0 | 100 | 100 | 75.0 | 100 | Not Scored |
| Swelling | 50.0 | 83.3 | 54.2 | 61.7 | 66.7 | 100 |
| Spreading | 66.7 | 100 | 100 | 100 | 100 | 100 |

*[ ] Represents an increase in symptom level

TABLE 2.4

(Number of lesions presented by subjects in each treatment concentration)

| Patient # | 0% | 0.00083% | 0.0033% | 0.0067% |
|---|---|---|---|---|
| 1 | 2 | 3 | 2 | 2 |
| 2 | 1 | 3 | 1 | 2 |
| 3 | 4 | 7 | 2 | 3 |
| 4 | 5 | 2 | 1 | 1 |
| 5 | 2 |  | 7 |  |
| Total Patients/Conc. | 5 | 4 | 5 | 4 |
| Mean lesions/patient | 2.8 | 3.75 | 2.6 | 2.0 |

TABLE 2.5

(Mean percentage decay rates of lesions for each patient in each treatment concentration)

| Patient # | 0% | 0.00083% | 0.0033% | 0.0067% |
|---|---|---|---|---|
| 1 | −120.2 | −2.2 | 33.1 | 54.5 |
| 2 | 2.7 | 28.4 | 13.9 | 79.9 |
| 3 | 2.5 | 27.1 | 23.6 | 67.0 |
| 4 | 2.0 | 38.9 | 32.3 | 16.5 |
| 5 | −11.3 |  | −17.8 |  |
| Conc. mean | −24.9 | 23.1 | 24.1 | 54.4 |
| Conc. std. dev. | 28.86 | 3.11 | 7.30 | 7.48 |

*Negative signs indicate growth rates

EXAMPLE 3—HERPES LABIALIS—THIRD STUDY

An additional gel concentration (0.0275%) was used on two patients for active herpes labialis lesions. As with the original Example 1 study, a standardized decay rate per 24 hours was calculated for each patient and compared to the two patients who received the placebo gel and who had the best treatment results of all of the patients treated with the placebo gel. The calculated, standardized decay rate for each of the four patients and their respective gel concentrations are shown in the table below.

TABLE 3.1

| % Gel Conc. | Standardized Decay Rate/24 hrs |
|---|---|
| 0.0 | 2.7 |
| 0.0 | 2.5 |
| 0.0275 | 56.55 |
| 0.0275 | 36.36 |

In order to determine if the differences in standardized decay rates for the four patients is significant, a statistical analysis was performed. An analysis of variance with treatment group (gel concentration) as a between-subjects factor. The result of the omnibus test was $F(1,2)=18.87$. The critical F value for 1 and 2 degrees of freedom at the 0.05 significance level is 18.51. Thus a significant overall treatment effect occurred as measured by lesion decay rates.

The results of this follow-up study show that, even with a small sample population, the gel concentration, 0.0275%, demonstrated statistically significant ($p<0.05$) differences in treatment results when compared to the placebo gel when measuring lesion decay rates.

EXAMPLE 4—HERPES GENITALIS

The safety and effectiveness of IEP administered topically to herpes genitalis lesions was evaluated in 4 patients. Subjects with active lesions were randomly assigned to use one of three IEP gel concentrations of 0.0%, 0.015%, and 0.0275% by weight of active ingredient. Treatment consisted of topical application three times a day for a period of five days. There were no untoward reactions in any treatment group. The percent reduction in complete healing time as compared to a usual episode was evaluated grouping the two patients who received active gel concentrations together and comparing to the two patients receiving placebo gel.

Each patient was contacted daily for 5 days for his or her estimate of the symptomatic relief of 6 common symptoms associated with genital herpes as well as the patient's interpretation of total healing of the episode. In an attempt to quantify responses, patients were asked to rate each symptom on a scale of 0 to 5 with 0 representing no evidence of the symptom and 5 representing the worst or most prominent evidence of the symptom ever for the patient. Subject compliance with the study regimen and the use of other medications was also assessed.

Table 4.1 summarizes each patient's estimate of the time to complete healing in days for a usual genital herpes episode and the time to complete healing in days for the episode treated in this study.

TABLE 4.1

| Patient # | Usual Healing Time (Days) | Healing Time (Days) |
|---|---|---|
| 600 | 10 | 12 |
| 601 | 7 | 7 |
| 603 | 7 | 1 |
| 604 | 7 | 3.5 |

Table 4.2 shows calculations using the data in Table 4.1 to determine the percent reduction in complete healing time for the episode treated in the study compared to the patient's usual herpes genitalis episode. These data show that, even in a small sample population, the time to complete healing was clearly reduced in patients treated with gel containing the active ingredient. The respective, randomly assigned gel concentrations for each patient are also shown in Table 4.2.

TABLE 4.2

| Patient # | % IEP Gel | Reduction In Complete Healing Time |
|---|---|---|
| 600 | 0.0 | 0% |
| 601 | 0.0 | 0% |
| 603 | 0.0275 | 85% |
| 604 | 0.015 | 50% |

Subjective data for the four patients is summarized in Table 4.3 for the only two symptoms in common for all four patients for each day of treatment while participating in the study. This data would suggest that symptomatic relief was better for the gels containing active concentration of IEP as compared to placebo (0.0%) gel.

TABLE 4.3

| Patient # | % IEP | LOCAL PAIN | | | | | BURNING | | | | |
|---|---|---|---|---|---|---|---|---|---|---|---|
| 600 | 0.0 | 4 | 4 | 4 | 4 | — | 4 | 3 | 4 | 4 | — |
| 601 | 0.0 | 3 | 3 | 3 | 3 | 3 | 3 | 3 | 4 | 4 | 3 |
| 603 | 0.0275 | 3 | 0 | 0 | 0 | 0 | 3 | 0 | 0 | 0 | 0 |
| 604 | 0.015 | 4 | 2 | 2 | 0 | 0 | 3 | 1 | 0 | 0 | 0 |

In order to determine if observed differences in complete healing time were significant, a statistical analysis of the percent reduction in complete healing time as compared to a usual herpes genitalis episode was performed. The values for percent reduction in complete healing time in Table 4.2 were subjected to an analysis of variance with treatment group as a between-subjects factor. Because of the small number of subjects in Treatment Concentration 0.015% and 0.0275%, the results from these two groups were combined and compared to the placebo. The results of the omnibus test was $F(1,2)=18.78$. The critical F value at the 0.05 significance level is 18.51. Thus, a significant overall treatment effect occurred as measured by the percent reduction in complete healing time as compared to a usual herpes genitalis episode.

The results of this study show that when compared with the placebo, both active concentrations of active ingredient showed a decrease in complete healing time as compared to a usual herpes genitalis episode. A statistical comparison of results between the placebo and the combined results of the active ingredient groups demonstrated significant ($p<0.05$) differences in treatment results when measuring the percent reduction in complete healing time as compared to the healing time of a usual herpes genitalis episode.

EXAMPLE 5—PRESSURE SORES (DECUBITUS ULCERS)

The safety and effectiveness of IEP administered topically to pressure sores (decubitus ulcers) was evaluated in 8 patients. Subjects were randomly assigned to one of four IEP gel concentrations of 0.0%, 0.0045%, 0.0067%, and 0.009% by weight with a total of two patients assigned to each gel concentration. Treatment included standardized decubitus ulcer care for all pressure sores as determined by the protocol for the study. In addition, topical application of all gel concentrations to their respective, randomly assigned patients occurred once daily and continued until complete healing or a definite failure to heal was demonstrated. There were no untoward effects seen by any patient. The mean percent reduction in lesion area per week generally showed more rapid reduction with increasing active ingredient concentration.

Prospective subjects were considered for the study if their pressure sores (decubitus ulcers) were free from infection and either a Stage I or a Stage II lesion.

Patients were randomly assigned to one of four active ingredient levels being evaluated. This random assignment was made in groups of four patients to assure that each gel concentration was represented once in each group of four. Assignment of subjects to the four gel concentrations was unknown to the investigator.

The topical application of all gel concentrations to their respective, randomly assigned patients occurred once daily following careful rinsing of the pressure sore with sterile normal saline. After application of the appropriate gel concentration, each pressure sore was covered with a bio-occlusive dressing to minimize wound contamination. Treatment continued daily until complete healing or a definite failure to heal was demonstrated.

Clinical evaluation included weekly classification of the stage of the pressure sores, the size and depth of the sores, the color, signs of infection (if present), odor (if present), and patient cooperation with treatment.

Table 5.1 on the next page lists the patient control numbers assigned to each patient who participated in the study and the gel concentrations those patients were randomly assigned to.

TABLE 5.1

| Patient # | % IEP |
|---|---|
| 405 | 0.0 |
| 411 | 0.0 |
| 400 | 0.0045 |
| 402 | 0.0045 |
| 406 | 0.0069 |
| 408 | 0.0069 |
| 403 | 0.009 |
| 404 | 0.009 |

Table 5.2 lists the percent reduction in area of the lesions measured for each of the eight patients who participated in the study for each week of their participation. For patients with more than one lesion treated, an average value for that patient was calculated and is shown in Table 5.2.

TABLE 5.2

(Percent Reduction in Area from Original Size)

| End of Treatment Week Number | Patient # | | | | | | | |
|---|---|---|---|---|---|---|---|---|
| | 405 | 411 | 400 | 402 | 406 | 408 | 403 | 404 |
| 1 | [25.0] | 0 | 28.5 | 29.8 | 48.6 | 55.6 | 66.7 | 56.5 |
| 2 | 0 | [25.0] | 33.6 | 66.6 | 77.1 | 60.0 | 100.0 | 56.5 |
| 3 | 25.0 | 0 | 51.6 | 72.8 | 77.1 | 78.2 | | 100.0 |
| 4 | 0 | 0 | 71.7 | 84.9 | 100 | 81.3 | | |
| 5 | Disc. | Disc. | 78.8 | 90.1 | | 84.4 | | |
| 6 | | | 87.0 | 95.6 | | 88.9 | | |
| 7 | | | 91.4 | 97.5 | | 100 | | |
| 8 | | | 92.3 | 99.4 | | | | |
| 9 | | | 92.3 | 99.4 | | | | |
| 10 | | | | 99.4 | | | | |

*[ ] = represents an increase in percentage
Disc. = treatment discontinued

To more effectively show the rate of lesion decay, the mean percent reduction in area from original size per week was calculated for each patient and is shown in Table 5.3. The patient's randomly assigned gel concentration is also shown in Table 5.3.

TABLE 5.3

| Patient # | Gel Conc. (%) | Mean Percent Reduction/Week |
|---|---|---|
| 405 | 0.0 | 0.0 |
| 411 | 0.0 | 0.0 |
| 400 | 0.0045 | 10.3 |
| 402 | 0.0045 | 12.1 |
| 406 | 0.0069 | 25.0 |
| 408 | 0.0069 | 14.3 |
| 403 | 0.009 | 50.0 |
| 404 | 0.009 | 40.0 |

In order to determine if these observed differences were significant, a statistical analysis of the mean percent reduction in area from the original lesion size per week values contained in Table 5.3 were subjected to an analysis of variance with treatment group as a between-subjects factor. The results of the omnibus test was $F(3,6)=26.87$. The critical F value for 3 and 6 degrees of freedom at the 0.01 significance level is 9.78. Thus, a highly significant treatment effect occurred as measured by mean percent reduction in area from original lesion size per week. Of particular interest was whether the placebo group was significantly different from the group receiving the highest level of active ingredient (0.009%). A follow-up test was performed to compare just the values from these two gel concentration groups. The result was $F(1,2)=81.00$. The critical F value at the 0.05 significance level is 18.51. Hence, the two groups were significantly different.

The results of this study show that with increasing concentration of active ingredient, there generally was an increase in the percentage of reduction in lesion area as compared to the original lesion area when considering the same treatment period. An analysis of variance was calculated comparing all active gel concentrations to the placebo which demonstrated highly significant ($p<0.01$) differences in treatment results. A statistical comparison in mean percent reduction in area per week between the placebo gel (0%) and highest level of the active ingredient (0.009%) showed that IEP was statistically significantly more effective ($p<0.05$) in reducing the size of pressure sores (decubitus ulcers).

EXAMPLE 6—VARICELLA ZOSTER (CHICKENPOX) LESIONS

The safety and effectiveness of IEP administered topically to Varicella zoster (chickenpox) lesions was evaluated in 4 patients. Subjects with active lesions were randomly assigned to use one of three IEP gel concentrations of 0.0%, 0.0067%, and 0.009% by weight of active ingredient. Treatment consisted of topical application three times a day for a period of five days. There were no untoward reactions in any treatment group. The mean percent reduction in complete healing time per average pox lesion was evaluated grouping the two patients who received active gel concentrations together and comparing to the two patients receiving placebo gel.

Prospective subjects were considered for the study if they had an active episode of Varicella zoster (chickenpox).

Subjects were assigned randomly to one of three active ingredient levels being evaluated, 0.0%, 0.0067% and 0.009% by weight of active ingredient. This random assignment of subjects to gel concentrations utilized treatment labels stating Concentration A, Concentration B, and Concentration C respectively to insure blindness on the part of the investigator.

Each patient was contacted daily for 5 days for his or her estimate of the symptomatic relief of any symptoms associated with Varicella zoster (chickenpox) as well as the patient's interpretation of total healing of the episode in addition to the patient's description of the lesions present. In an attempt to quantify responses, patients were asked to rate each symptom each day on a scale of 0 to 5 with 0 representing no evidence of the symptom and 5 representing to worst or most prominent evidence of the symptom ever for the patient. Subject compliance with the study regimen and the use of other medications was also assessed.

Lesions were monitored for the usual progression of the typical stages seen with Varicella zoster. Typical chickenpox begins as crops of small, red papules that almost immediately develop into clear, "tear drop" vesicles on an erythematous base which are usually not umbilicated. The lesions initially contain clear fluid, but within 24 hours the contents become cloudy. Once this occurs, the vesicles are easily broken and become scabbed. Successive crops of lesions appear for 3 to 4 days.

Table 6.1 summarizes the mean of each patient's estimate of the time to complete healing in days for his or her average varicella zoster lesions. The respective, randomly assigned gel concentrations for each patient are also shown in Table 6.1.

TABLE 6.1

| Patient # | Gel. Conc. (%) | Mean Time to Lesion Healing (days) |
|---|---|---|
| 10 | 0.0067 | 3.5 |
| 11 | 0.009 | 2.5 |
| 12 | 0.0 | 7 |
| 14 | 0.0 | 7 |

Table 6.2 shows calculations using the data in Table 6.1 to determine the percent reduction in complete healing time for patients treated with active gel (0.0067% or 0.009%) in the study compared to the patients treated with placebo gel (0.0%). These data show that, even in a small sample population, the percent reduction in complete healing time per lesion was clearly better in patients treated with gel containing the active ingredient.

TABLE 6.2

| Patient # | % IEP | Mean % Reduction In Healing Time per Lesion |
|---|---|---|
| 10 | 0.0067 | 50.0 |
| 11 | 0.009 | 64.28 |
| 12 | 0.0 | 0.0 |
| 14 | 0.0 | 0.0 |

Additionally important but not quantitative in nature for statistical purposes is the fact that lesions treated with the active gel concentrations (0.0067% and 0.009%) did not progress through the usual progression of lesions stages. These lesions, if treated in the papule form, did not produce vesicles and, thus did not rupture and form scabs. Lesions that had progressed to the vesicle stage before treatment had begun, dried up and the vesicle portion of the lesion disappeared. Again, since there were no vesicles to rupture, scabs did not form.

Subjective data for the four patients is summarized in Table 6.3 for the only two symptoms in common for all four patients for each day of treatment while participating in the study. This data would suggest that symptomatic relief was better for the gels containing active concentration of IEP as compared to placebo gel.

TABLE 6.3

| Patient # | % IEP | LOCAL PAIN | | | | | ITCHING | | | |
|---|---|---|---|---|---|---|---|---|---|---|
| 10 | 0.0067 | 2 | 1 | 0 | 0 | 0 | 2 | 0 | 0 | 0 |
| 11 | 0.009 | 3 | 1 | 0 | 0 | 0 | 2 | 0 | 0 | 0 |
| 12 | 0.0 | 3 | 3 | 3 | 4 | 3 | 2 | 3 | 4 | 4 | 4 |
| 14 | 0.0 | 4 | 4 | 4 | 4 | 3 | 4 | 4 | 4 | 4 |

In order to determine if observed differences in mean percent reduction in complete healing time per lesion were significant, a statistical analysis of the mean percent reduction in complete healing time per lesion values in Table 6.2 were subjected to an analysis of variance with treatment group as a between-subjects factor. Because of the small number of subjects in Treatment Concentration 0.0067% and 0.009%, the results from these two groups were combined and compared to the placebo. The results of the omnibus test was $F(1,2)=64.04$. The critical F value at the 0.05 significance level is 18.51. Thus, a significant overall treatment effect occurred as measured by the mean percent reduction in complete healing time per lesion when comparing the healing time results of the two patients treated with active gel combined and the two patients treated with placebo gel.

The results of this study show that when compared with the placebo, both active concentrations of active ingredient showed a decrease in mean complete healing time per Varicella zoster (chickenpox) lesion. A statistical comparison of results between the placebo and the combined results of the active ingredient groups demonstrated significant ($p<0.05$) differences in treatment results when measuring the mean percent reduction in complete healing time per Varicella zoster (chickenpox) lesion. Additionally, it was found that the gels containing active ingredient appeared to prevent the normal progression of lesion stages, thus preventing scabbing and decreasing the healing time for Varicella zoster (chickenpox) lesions treated with active ingredient.

EXAMPLE 7—HERPES ZOSTER (SHINGLES) LESIONS

The safety and effectiveness of IEP administered topically to shingles lesions was evaluated in 4 patients. Subjects with active lesions were randomly assigned to use one of two IEP gel concentrations of 0.0% and 0.015% by weight of active ingredient. Treatment consisted of topical application three times a day until healing or a failure to heal was demonstrated. There were no untoward reactions in any treatment group. The percent reduction in complete healing time as compared to a usual episode was evaluated comparing the two patients who received active gel concentrations to the two patients receiving placebo gel. Prospective subjects were considered for the study only if they had experienced two or more episodes of herpes zoster (shingles) lesions per year. Subjects were assigned randomly to one of two active ingredient levels being evaluated, 0.0% and 0.015% by weight of active ingredient.

Each patient was contacted weekly for his or her estimate of the symptomatic relief of 2 common symptoms associated with herpes zoster (shingles) as well as the patient's interpretation of total healing of the episode. In an attempt to quantify responses, patients were asked to rate each symptom on a scale of 0 to 5 with 0 representing no evidence of the symptom and 5 representing the worst or most prominent evidence of the symptom ever for the patient. Subject compliance with the study regimen and the use of other medications was also assessed.

No untoward events or significant complications associated with the use of any of the two test compositions were observed in this study.

Table 7.1 summarizes each patient's estimate of the time to complete healing in days for a usual herpes zoster (shingles) episode and the time to complete healing in days for the episode treated in this study.

TABLE 7.1

| Patient # | Usual Healing Time (days) | Healing Time (days) |
|---|---|---|
| 500 | 49 | 21 |
| 501 | 35 | 18 |
| 502 | 28 | 29 |
| 503 | 42 | 40 |

Table 7.2 shows calculations using the data in Table 7.1 to determine the percent reduction in complete healing time for the episode treated in the study compared to the patient's usual herpes zoster (shingles) episode. These data show that, even in a small sample population, the time to complete healing was clearly reduced in patients treated with gel containing the active ingredient. The respective, randomly assigned gel concentrations for each patient are also shown in Table 7.2.

TABLE 7.2

| Patient # | % Gel Conc. | Percentage Reduction in Healing Time |
|---|---|---|
| 500 | 0.015 | 57.1 |
| 501 | 0.015 | 48.6 |
| 502 | 0.0 | [3.6] |
| 503 | 0.0 | 4.8 |

[ ] represents an increase rather than a decrease in healing time

Subjective data for the four patients is summarized in Table 7.3 for the two symptoms evaluated by all four patients for each week for the first 5 weeks of treatment while participating in the study. This data would suggest that symptomatic relief was better for the gels containing active concentration of IEP as compared to placebo (0.0%) gel.

TABLE 7.3

| Patient # | % IEP | LOCAL PAIN | BURNING |
|---|---|---|---|
| 500 | 0.015 | 4 2 0 0 0 | 4 3 0 0 0 |
| 501 | 0.015 | 3 2 0 0 0 | 3 3 0 0 0 |
| 502 | 0.00 | 3 4 3 1 0 | 3 3 2 1 0 |
| 503 | 0.0 | 4 4 3 3 2 | 4 3 3 2 2 |

In order to determine if observed differences in complete healing time were significant, a statistical analysis of the percent reduction in complete healing time as compared to a usual herpes zoster (shingles) episode was performed. The values for percent reduction in complete healing time in Table 7.2 were subjected to an analysis of variance with treatment group as a between-subjects factor. The results for the two active gel patients were compared to the two patients who received placebo gel. The results of the omnibus test was $F(1,2)=76.45$. The critical F value the 0.05 significance level is 18.51. Thus, a significant overall treatment effect occurred as measured by the pert reduction in complete healing time as compared to a usual herpes zoster (shingles) episode.

The results of this study show that when compared with the placebo, the active concentration (0.015%) showed a decrease in complete healing time as compared to a usual herpes zoster (shingles) episode. A statistical comparison of results between the placebo and the active gel demonstrated significant ($p<0.05$) differences in treatment results when measuring the percent reduction in complete healing time as compared to the healing time of a usual herpes zoster episode.

EXAMPLE 8—APHTHOUS STOMATITIS LESIONS

The safety and effectiveness of 1H-Imidazole-4-Ethanamine Phosphate administered topically to aphthous stomatitis lesions (canker sores) was evaluated in 10 patients. Subjects with active lesions were randomly assigned to use one of three 1H-Imidazole-4-Ethanamine Phosphate concentrations of 0.0% (Group B), 0.0067% (Group C) and 0.0275% (Group E) by weight of active ingredient. Treatment consisted of topical application five times per day for a period of five days, with daily evaluation by patient and clinician. Lesion decay rates (decrease in lesion size over time) of Groups C and E were grouped together and compared to Group B, the placebo Group. An analysis of variance of the placebo and active treatment results showed the active treatment to be significantly more effective ($p<0.01$) in reducing lesion size over time.

Prospective subjects were considered for the study, if they had experienced two or more episodes of aphthous stomatitis lesions in the prior year, and had active aphthous stomatitis lesions at the time of recruitment.

Patients were assigned randomly to one of the three active ingredient levels being evaluated. Assignment of subjects within groups to the three concentrations was unknown to the investigator.

Subjects were instructed to begin application immediately, to topically apply the product five times a day, and to record exact times of application.

Clinical evaluation included daily classification of the phase or stage of lesions and size, number and location of lesions and subject compliance with the study regimen and use of other medication. Photographic records of lesion progression or degression were made for each subject at each visit.

No untoward events or significant complications we observed in this study.

Table 8.1 summarizes the average percent effective of each gel concentration in reducing lesion size (in mm) as a function of time when compared to initial measurement taken on entrance to the study. These data show that, with the small sample population, the rate of lesion decrease clearly was more rapid with both groups treated with gel containing the active ingredient.

TABLE 8.1

(Average percent reduction in lesions from original size)

| % Gel Conc. | 24 Hrs. | 48 Hrs. | 72 Hrs. | 96 Hrs. |
|---|---|---|---|---|
| 0% (Gel B) | *[44.8] | *[29.2] | *[54.5] | *[59.3] |
| 0.0067% (Gel C) | 64.6 | 90.0 | 97.4 | 98.5 |
| 0.0275% (Gel E) | 54.5 | 83.1 | 95.1 | 100 |

*[ ] represent % growth rather than reduction

Reduction in lesion area or decay rate over time as function of concentration of active ingredient was calculated for subjects in each of the three treatment groups. Table 8.2 shows the number of subjects in each group and the number of lesions presented by each subject. The decay rate was calculated by first computing the the percentage decrease in size of the lesion over time and when standardizing the decay rate over an exact 24 hour period. This standardization allowed a more meaningful statistical comparison of and subsequent inferences from decay rates across treatments.

TABLE 8.2

(Number of lesions presented by subjects in each treatment conc.)

| # Patients | 0% | 0.0067% | 0.0275% |
|---|---|---|---|
| 1 | 2 | 1 | 1 |
| 2 | 1 | 1 | 4 |
| 3 | 1 | 5 | |
| 4 | 2 | | |
| 5 | 1 | | |
| Total Patients/Conc. | 5 | 3 | 2 |
| Mean Lesions/Patient | 1.4 | 2.33 | 2.5 |

After calculating a standardized decay rate per lesion, an average decay rate for each subject was computed. Decay rates were computed for each lesion assessment and then averaged across assessments; for patients with multiple lesions, decay rates were averaged across lesions. Table 8.3 shows the mean percentage decay rates for 10 subjects across three treatment groups. Comparing the mean decay rates of the three treatment groups shown in Table 8.3 with the mean percentage decay rates for each subject, it appeared that treatment groups varied in lesion decay rates.

TABLE 8.3

(Mean percentage decay rates of lesions for each patient in each treatment conc.)

| # Patients | 0% | 0.0067% | 0.0275% |
|---|---|---|---|
| 1 | −14.0 | 100.0 | 104.0 |
| 2 | −52.4 | 53.8 | 62.9 |
| 3 | 28.2 | 68.4 | |
| 4 | −22.5 | | |
| 5 | −00.8 | | |
| Conc. mean | −12.3 | 74.1 | 83.5 |
| Conc. std. dev. | 08.7 | 05.6 | 08.5 |

*Negative signs indicate growth rates

In order to determine if these observed differences were significant, a statistical analysis of the decay rates was performed. Subject decay rates were subjected to an analysis of variance (ANOVA) with treatment group as a between-subjects factor. Because of the small number of subjects in Treatment Concentrations C and E (0.0067% and 0.0275%, respectively), the results were combined and compared to the placebo. The results of the omnibus test was $F(1,8)=29.24$. Thus, a significant overall treatment effect ($p<0.01$) occurred as measured by lesion decay rates.

The results of this study show that compared with the placebo, both concentrations of active ingredient showed an increase in the decay rate (diminishment) of the lesions of subjects in the respective treatment groups. A statistical comparison of results between the placebo and the combined results of the active ingredient groups showed that 1H-Imidazole-4-Ethanamine Phosphate was more effective at a highly significant level ($p<0.01$) in reducing the size of lesions for aphthous stomatitis patients.

EXAMPLE 9—ORAL MUCOSITIS (STOMATITIS) SECONDARY TO CHEMOTHERAPY

The safety and effectiveness of IEP administered topically, intraorally to chemotherapy patients with secondary mucositis (stomatitis) was evaluated in 9 patients. Subjects were randomly assigned to one of three IEP gel concentrations of 0.0%, 0.0045%, and 0.0275% by weight of active ingredient. Treatment consisted of topical, intraoral application by swishing one teaspoonful of the patient's respective randomly assigned gel concentration five times a day until complete healing or a definite failure to heal was demonstrated. There were no untoward effects seen by any patient. Decrease in total amount of oral involvement with mucositis (stomatitis) was calculated as a percent reduction from the original involvement per day, and generally there was a greater decrease in oral mucous membrane involvement more rapidly with increasing active ingredient concentration. An analysis of variance was calculated comparing both active gel concentrations to the placebo which demonstrated highly significant ($p<0.01$) differences in treatment results.

Prospective subjects were considered for the study if their mucositis (stomatitis) was diagnosed by their oncologist as secondary to their chemotherapy and if their oncologist recommended them as candidates for the study.

Patients were randomly assigned to one of three active ingredient levels being evaluated. This random assignment was made in groups of three patients to assure that each gel concentration was represented in each group of three.

Following diagnosis and recommendation of oral mucositis patients by their oncologists, qualified participants were instructed to topically, intraorally apply one teaspoonful of their respective, randomly assigned gel by swishing and holding the gel in their mouth for 2 minutes and then expectorating the gel. Each patient was to perform this application of the gel five times a day until complete healing or a definite failure to heal was demonstrated.

Evaluation of the extent of the oral mucous membrane involvement was based on each patient's estimate of this involvement (as a percentage) of the entire oral mucous membranes and each patient was contacted daily for this estimate as well as his or her estimate of the symptomatic relief of 5 common oral symptoms associated with mucositis (stomatitis) secondary to chemotherapy. In an attempt to quantify responses, patients were asked to rate each symptom each day on a scale of 0 to 5 with 0 representing no evidence of the symptom and 5 representing the worst or most prominent evidence of the symptom ever for the patient.

Patient compliance with the study regimen and the use of other medications or treatments was also evaluated.

Tables 9.1, 9.2, and 9.3 list patient estimates of the percentage of total oral mucous membranes involved with their mucositis for each day of treatment. Data for gel concentrations 0.0%, 0.0045%, and 0.0275% has been separated into Tables 9.1, 9.2, and 9.3 respectively.

TABLE 9.1

(Concentration = 0%)
Percent of Mouth that Lesions Occupy Each Day of Treatment

| Patient # | Day | | | | | | |
|---|---|---|---|---|---|---|---|
| | 1 | 2 | 3 | 4 | 5 | 6 | 7 |
| 107 | 40 | 40 | 40 | 40 | 40 | — | — |
| 103 | 50 | 50 | 50 | 50 | 50 | — | — |
| 101 | 35 | 35 | 35 | 35 | 35 | 35 | 35 |

TABLE 9.2

(Concentration = 0.0045%)
Percent of Mouth that Lesions Occupy
Each Day of Treatment

| Patient # | Day | | | | | | |
|---|---|---|---|---|---|---|---|
| | 1 | 2 | 3 | 4 | 5 | 6 | 7 |
| 112 | 50 | — | — | 25 | — | 5 | — |
| 108 | 3 | 2.5 | 2 | 1 | 0 | 0 | 0 |
| 103 | 25 | 25 | 25 | 0 | 0 | 0 | 0 |

TABLE 9.3

(Concentration = 0.0275%)
Percent of Mouth that Lesions Occupy
Each Day of Treatment

| Patient # | Day | | | | | | |
|---|---|---|---|---|---|---|---|
| | 1 | 2 | 3 | 4 | 5 | 6 | 7 |
| 109 | 25 | 25 | 0 | 0 | 0 | 0 | 0 |
| 104 | 25 | 25 | 25 | 0 | 0 | 0 | 0 |
| 103 | 50 | 30 | 25 | 0 | 0 | 0 | 0 |

Table 9.4 shows the mean daily percentage reduction from the original oral involvement for each patient who participated in the study as calculated from the data in Tables 9.1, 9.2, and 9.3. The respective gel concentration is also shown for each patient in Table 9.4.

TABLE 9.4

(Mean Daily Reduction (%) from Original Oral
Mucous Membrane Involvement Per Patient)

| Patient # | % IEP | Mean Percent Reduction From Original Involvement Per Day |
|---|---|---|
| 107 | 0.0 | 0.0 |
| 103 | 0.0 | 0.0 |
| 101 | 0.0 | 0.0 |
| 112 | 0.0045 | 18.0 |
| 108 | 0.0045 | 25.0 |
| 105 | 0.0045 | 33.3 |
| 109 | 0.0275 | 50.0 |
| 104 | 0.0275 | 33.3 |
| 103 | 0.0275 | 33.3 |

From the values listed in Table 9.4, a mean daily reduction (in percentage) from the original amount of oral mucous membrane involvement was calculated for each gel concentration group and is shown in Table 9.5.

TABLE 9.5

(Mean Daily Reduction (%) From Original Mucous Membrane
Involvement Per Gel Concentration Group

| Gel Conc. | Mean Percent Reduction from original Per Day |
|---|---|
| 0.0 | 0.0 |
| 0.0045 | 25.4 |
| 0.0275 | 38.9 |

In order to determine if these observed differences were significant, a statistical analysis of the mean percent reduction in oral mucous membrane involvement from the original involvement per day values contained in Table 9.4 were subjected to an analysis of variance with treatment group as a between-subjects factor. The result of the omnibus test was $F(2,7)=23.20$. The critical F value for 2 and 7 degrees of freedom at the 0.01 significance level is 9.55. Thus, a highly significant treatment effect occurred as measured by mean percent reduction in oral mucous membrane involvement from original involvement per day. Of particular interest was whether the placebo group was significantly different from the group receiving the highest level of active ingredient (0.0275%). A follow-up test was performed to compare just the values from these two gel concentration groups. The result was $F(1,4)=24.92$. The critical F value at the 0.01 significance level for 1 and 4 degrees of freedom is 21.20. Hence, the two groups demonstrated highly significant differences in treatment results.

Patient variation in subjective interpretation of discomfort left only 2 of the original 5 common oral symptoms that were consistent throughout all patients, thus allowing for comparisons between gel concentration groups. The mean percent reduction per day from the original response for patients within each gel concentration group for relief of patient discomfort when eating or drinking were calculated and are listed in Table 9.6. The mean percent reduction per day for patients within each gel concentration group for relief of discomfort associated wit routine oral care were calculated and are listed in Table 9.7.

TABLE 9.6

| % IEP | Mean Percent Reduction Per Day in Discomfort with Food/Drink | | Mean % Reduction in Symptom |
|---|---|---|---|
| 0.0 | 8.3 | [25.0] | 0.0 | [5.6] |
| 0.0045 | 100.0 | 33.3 | 33.3 | 55.6 |
| 0.0275 | 100.0 | 25.0 | 33.3 | 52.8 |

[ ] = represents increase in symptom

TABLE 9.7

| Gel Conc. | Mean Percent Reduction Per Day in Discomfort with Food/Drink | | Mean % Reduction in Symptom |
|---|---|---|---|
| 0.0 | 0.0 | 5.0 | 0.0 | 1.7 |
| 0.0045 | 100.0 | 25.0 | 50.0 | 58.3 |
| 0.0275 | 100.0 | 50.0 | 100.0 | 83.3 |

Of primary interest is the statistical analysis of the mean percent reduction per day of both symptoms, patient discomfort when eating or drinking and patient discomfort with routine oral care. This analysis was performed for both symptoms from the values listed in Table 9.6 and Table 9.7 comparing the placebo gel (0.0%) and the highest gel concentration (0.0275%) by subjecting those values to an analysis of variance.

The result of the omnibus test for the first symptom, discomfort when eating or drinking, was $F(2,4)=20.70$. The critical F value for 2 and 4 degrees of freedom at the 0.01 significance level is 18.00. Thus, the two gel concentration groups (0.0% and 0.0275%) demonstrated highly significant differences in the relief of patient discomfort associated with eating or drinking.

The result of the omnibus test for the second symptom, discomfort with routine oral care, was $F(2,4)=23.76$. The critical F value for 2 and 4 degrees of freedom at the 0.01 significance level is 18.00. Hence, the two gel concentration groups (0.0% and 0.0275%) demonstrated highly significant differences in the relief of patient discomfort associated with routine oral care.

The results of this study show that with increasing concentration of active ingredient, there generally was a greater percentage reduction in oral mucous membrane involvement from original involvement per day of the mucositis (stomatitis) found secondary to chemotherapy. An analysis of variance was calculated comparing all gel concentrations which demonstrated highly significant (p<0.01) differences in treatment results when measuring actual reduction in the amount of oral mucous membrane involvement. A statistical comparison of results between placebo and highest level of active ingredient (0.0275%) showed highly statistically significant (p<0.01) differences in treatment results when measuring actual reduction in the amount of oral mucous membrane involvement. Follow-up tests of significance were performed on data and calculations from the subjective analysis of the symptomatic relief of two common symptoms associated with oral mucositis (stomatitis) secondary to chemotherapy. Again, the highest level of active ingredient (0.0275%) proved statistically highly significantly different when compared to the placebo gel for the symptomatic relief of these two symptoms.

EXAMPLE 10—PHOTODERMATITIS (SECOND DEGREE SUNBURN)

The safety and efficacy of IEP administered topically to Photodermatitis (second degree sunburn) demonstrating blister formation was evaluated. The subject was exposed to sufficient irradiation from the sun (approximately 2½ hours) to produce a sunburn which resulted in blister formation as well as deep reddening of the epidermis on the subject's back. The subject's back was divided into four quadrants for lotion or gel application purposes and each quadrant was randomly assigned one of three IEP lotion or gel concentrations, 0% (placebo lotion or gel ), 0.0045% and 0.0067% by weight of active ingredient, with 2 of the four quadrants receiving the 0% lotion or gel. There were no untoward effects in any treatment group. The rate of blister formation for each quadrant (total number of blisters per total time) was calculated from the actual count of blisters per quadrant at 65 hours post irradiation and was found to be less with increasing concentration of IEP.

The subject selected for the study had not had prolonged exposure to the sun for more than 1 year and his history indicated that he readily and predictably sunburned when exposed for 2–3 hours sunlight on first exposure to the sun each summer.

After the subject was exposed to sufficient irradiation from the sun (approximately 2½ hours) to produce a Photodermatitis (sunburn) which resulted in blister formation and deep reddening of the epidermis of the subject's back, the burned area was divided into four quadrants for lotion or gel application purposes. Each quadrant was randomly assigned to one of the three IEP lotion or gel concentrations, 0% (placebo lotion or gel, 0.0045% and 0.0067% by weight of active ingredient, with two of the four quadrants receiving the 0% lotion or gel. Individual bottles of the three lotion or gel concentrations, 0%, 0.0045%, and 0.0067%, were labeled Concentration C, Concentration A, and Concentration B respectively to ensure blindness on the part of the investigator.

Treatment consisted of topical application of all lotion or gel concentrations to their respective, randomly assigned quadrants every 30 minutes for the first 2 hours following the irradiation period, followed by lotion or gel applications every hour for four hours, then lotion or gel applications three times a day until 65 hours elapsed post irradiation. Photographs were taken during the treatment period and upon the formation of identifiable blisters, the numbers of blisters in each quadrant were recorded at three times during the treatment period with cessation of lotion or gel application and data collection at the 65 hours point as exfoliation (peeling) of the outer layers of the epidermis began at 70 hours.

Subjective evaluation involved an estimate of pain/discomfort following lotion or gel application in each quadrant as well as a comparative general discomfort level for each quadrant during the treatment period. Pain/discomfort was scored from 1 (none) to 5 (worst).

Table 10.1 shows the total number of blisters for each quadrant recorded at specific observation times (recorded as total hours post irradiation) during the treatment period. No untoward events or significant complications associated with the use of any of the test compositions were observed in this study.

TABLE 10.1

| QUADRANT | % IEP | TOTAL # OF BLISTERS AT 42 HRS | TOTAL # OF BLISTERS AT 52 HRS | TOTAL # OF BLISTERS AT 65 HRS |
|---|---|---|---|---|
| UPPER LEFT | 0.0067% | 2 | 2 | 10 |
| UPPER RIGHT | 0.0% | 12 | 12 | 28 |
| LOWER LEFT | 0.0% | 10 | 18 | 32 |
| LOWER RIGHT | 0.0045% | 7 | 7 | 14 |

Table 10.2 summarizes the total rate of blister formation for each quadrant as calculated from the total number of blisters present in each quadrant at 65 hours post irradiation. Generally, it can be seen that as the quantity of active ingredient increased, the rate of blister formation decreased.

TABLE 10.2

| QUADRANT | % IEP | Avg blisters/hr |
|---|---|---|
| UPPER LEFT | 0.0067% | 0.154 |
| UPPER RIGHT | 0.0% | 0.431 |
| LOWER LEFT | 0.0% | 0.492 |
| LOWER RIGHT | 0.0045% | 0.215 |

In order to determine if these observed differences were significant, a statistical analysis of the total rate of blister formation was performed. The total rates of blister formation were subjected to an analysis of variance with treatment group as a between-quadrants factor. Because of the small number of areas (quadrants) treated, and because the total rates of blister formation in the upper left quadrant and the lower right quadrant were similar, the data from these two quadrants were combined. A statistical test of the difference between the combined quadrants treated with active lotion or gel (0.0045% and 0.0067%) and the quadrants treated with placebo lotion or gel was performed. The results of the omnibus test was $F(1,2)=38.0$. The critical F value for 1 and 2 degrees of freedom at the 0.05 significance level is 18.51.

Subjective data for the four quadrants is summarized in Table 10.3 on the next page. Based on this data it would appear that symptomologic relief was better for the lotions or gels with an active concentration of IEP as compared to the placebo lotion or gel.

TABLE 10.3

| Quadrant | Lotion or Gel Conc. (%) | Discomfort on Lotion or Gel/Application | General Discomfort |
|---|---|---|---|
| UPPER LEFT | 0.0067% | 1 | 1 |
| UPPER RIGHT | 0.0% | 4 | 3 |
| LOWER LEFT | 0.0% | 5 | 4 |
| LOWER RIGHT | 0.0045% | 2 | 1 |

The results of this study show that a statistically significant treatment effect occurred between placebo and active lotion or gel, $p<0.05$ when treating Photodermatitis, as measured by total rate of blister formation over the total time of treatment. Subjective data suggests that the IEP decreases the discomfort of the Photodermatitis (sunburn) as well as decreasing the discomfort of application of the lotion or gel itself.

EXAMPLE 11—THERMAL BURN INJURIES

The safety and efficacy of IEP administered topically to thermal burn injuries intentionally induced under controlled circumstances was evaluated. The subject was exposed in six different areas to direct contact with a hair curling iron for two seconds duration in each area. The six areas were then randomly assigned one of three IEP gel concentrations, 0.0%, 0.0045%, and 0.009% by weight of active ingredient, with each gel concentration being assigned to two burn sites. The burn sites were monitored for four parameters of tissue damage associated burn injury for the first 22 hours and it was generally found that there was a more rapid resolution of the four parameters of tissue damage with increasing concentration of IEP.

The subject volunteered for this unusual study. He was allowed to perform the induction on himself. The subject was exposed to direct contact with a hair curling iron in six different areas (2 sites on each inner forearm and 1 site on each side of the abdominal wall) for 2 seconds at each site. The subject was older than 18 years of age, free from abnormalities or diseases of the skin, and free of allergies, asthma, emphysema, bronchitis, peptic ulcer disease, hiatal hernia or other intestinal disease.

After self-induction of the thermal burns at the six separate sites, each site was randomly assigned to one of three IEP gel concentrations by weight of active ingredient, 0.0% (placebo gel), 0.0045%, and 0.009% with each gel concentration being assigned to two burn sites. The three gel concentrations were labeled Concentration A, Concentration B, and Concentration C, respectively to insure blindness on the part of the subject, who was also the investigator.

Treatment consisted of topical application of all gel concentrations to their respective, randomly assigned burn site every 30 minutes for the first 2 hours, then every 3 hours for 3 more applications total. Photographs were taken during the treatment period. The burn sites were monitored for four parameters of tissue damage associated with burn injury for the first 22 hours. The burn sites were measured for 3 of the parameters of tissue damage at various times during the first 22 hours following burn induction. The zone of erythema surrounding each burn site was measured at the greatest width. The subject was asked to rate his discomfort for the fourth parameter of tissue damage on a scale of 0 to 5 with 0 representing absence of discomfort and 5 representing the highest level of discomfort.

There were no untoward events or significant complications associated with the use of any of the test compositions in this study.

Tables 11.1, 11.2, 11.3, and 11.4 show the data collected for the four parameters of tissue damage at various times during the first 22 hours of treatment following burn induction.

TABLE 11.1

(Height in mm of Swelling of Soft Tissue Surrounding Burn Site)

| Burn Site | % Gel Conc. | Hours | | | |
|---|---|---|---|---|---|
| | | 0 | 3.5 | 8 | 22 |
| A | 0.0 | 2 | 2 | 2 | 2 |
| E | 0.0 | 2 | 2 | 2 | 2 |

TABLE 11.1-continued (Height in mm of Swelling of Soft Tissue Surrounding Burn Site)

| Burn Site | % Gel Conc. | Hours | | | |
|---|---|---|---|---|---|
| | | 0 | 3.5 | 8 | 22 |
| B | 0.0045 | 2 | 1 | 1 | 0 |
| F | 0.0045 | 2 | 1 | 1 | 1 |
| D | 0.009 | 2 | 1 | 0 | 0 |
| C | 0.009 | 2 | 1 | 0 | 0 |

TABLE 11.2

(Subjective Evaluation of Tenderness on Palpation, (rated 0 to 5))

| Burn Site | % Gel Conc. | Hours | | | |
|---|---|---|---|---|---|
| | | 0 | 3.5 | 8 | 22 |
| A | 0.0 | 5 | 5 | 5 | 5 |
| E | 0.0 | 5 | 5 | 5 | 5 |
| B | 0.0045 | 5 | 3 | 2 | 2 |
| F | 0.0045 | 5 | 5 | 4 | 4 |
| D | 0.009 | 5 | 2 | 2 | 1 |
| C | 0.009 | 5 | 3 | 2 | 1 |

TABLE 11.3

(Height in mm of Blister)

| Burn Site | % Gel Con. | Hours | | | |
|---|---|---|---|---|---|
| | | 0 | 3.5 | 8 | 22 |
| A | 0.0 | 0 | 3 | 3 | 2.5 |
| E | 0.0 | 0 | 1.5 | 1.5 | 1.5 |
| B | 0.0045 | 0 | 3 | 2.5 | 1.5 |
| F | 0.0045 | 0 | 2 | 1.5 | 1 |
| D | 0.009 | 0 | 2 | 1 | 0.5 |
| C | 0.009 | 0 | 2 | 1 | 0 |

TABLE 11.4

(Zone of Erythema Surrounding Burn Site (mm))

| Burn Site | % Gel Conc. | Hours | | | |
|---|---|---|---|---|---|
| | | 0 | 3.5 | 8 | 22 |
| A | 0.0 | 8 | 6 | 6 | 4 |
| E | 0.0 | 10 | 7 | 6 | 4 |
| B | 0.0045 | 12 | 8 | 6 | 4 |
| F | 0.0045 | 8 | 4 | 3 | 1.5 |
| D | 0.009 | 9 | 6 | 4 | 2 |
| C | 0.009 | 8 | 4 | 3 | 2 |

From the values in Tables 11.1, 11.2, 11.3, and 11.4, the percent reduction in the specific parameter of tissue damage was calculated for each burn site at 22 hours following burn induction. The values shown in Table 11.5 list those calculations and represent the percent reduction in each parameter from the greatest value demonstrated by that burn site.

TABLE 11.5

| | (% Reduction in Tissue Damage at 22 Hours) | | | |
|---|---|---|---|---|
| Burn Site | Swelling of Surrounding Tissue | Tenderness on Palpation | Height of Blister | Zone of Erythema (mm) |
| A | 0 | 0 | 16.7 | 50.0 |
| E | 0 | 0 | 0 | 50.0 |
| B | 100.0 | 60.0 | 50.0 | 66.7 |
| F | 50.0 | 20.0 | 50.0 | 81.3 |
| D | 100.0 | 80.0 | 75.0 | 77.8 |
| C | 100.0 | 80.0 | 100.0 | 75.0 |

In order to determine if these observed differences were significant, a statistical analysis of the percent reduction of each tissue damage parameter was performed. The percent reduction values for each tissue damage parameter listed in Table 11.5 were subjected to an analysis of variance with treatment group as a between-burn site factor. The results of each omnibus test for each tissue damage parameter are listed in Table 11.6 which shows a comparison of all gel concentrations. As can be seen from Table 11.6, differences in treatment results were significant (p<0.05) for 3 of the 4 tissue damage parameters and were highly significant (p<0.01) for the fourth parameter.

TABLE 11.6

| (Analysis of Variance for Four Parameters of Tissue Damage (All Gel Concentrations)) | | | |
|---|---|---|---|
| Tissue Damage Parameter | Calculated Value of F(1,4) | Critical Value of F(1,4) | Significance Level (p<) |
| Swelling of Surr. Tissue | 13.0 | 7.71 | .05 |
| Tenderness on Palpation | 24.0 | 21.20 | .01 |
| Height of Blister | 20.78 | 7.71 | .05 |
| Zone of Erythema | 11.57 | 7.71 | .05 |

Of primary interest is the statistical analysis of the percent reduction at 22 hours post burn induction for each of the tissue damage parameters comparing the placebo gel to the highest level of active ingredient (0.009%). Table 11.7 lists the results of each statistical analysis performed for each tissue damage parameter for comparison of just the placebo and the highest gel concentration (0.009%). As can be seen in Table 11.7, differences in treatment results were highly significant (p<0.01) for 3 of the 4 tissue damage parameters and was significant (p<0.05) for the fourth.

TABLE 11.7

| (Analysis of Variance for Four Parameters of Tissue Damage (0.0% gel vs 0.009% gel)) | | | |
|---|---|---|---|
| Tissue Damage Parameter | Calculated Value of F(1,2) | Critical Value of F(1,2) | Significance Level (p<) |
| Swelling of Surr. Tissue | infinity | 98.50 | .01 |
| Tenderness on Palpation | infinity | 98.50 | .01 |
| Height of Blister | 27.69 | 18.51 | .05 |
| Zone of Erythema | 355.59 | 98.50 | .01 |

The results of this study show that with increasing concentration of active ingredient, there generally was a greater percentage reduction in parameters demonstrating tissue damage. A statistical comparison of results between all gel concentrations for four parameters of tissue damage showed significant (p<0.05) differences in treatment results for 3 of the 4 parameters when evaluating the four parameters of tissue damage. Calculations for the fourth parameter showed highly significant (p<0.01) differences in treatment results. A statistical comparison of the results between placebo and highest level of active ingredient (0.009%) demonstrated highly significant (p<0.01) differences for 3 of the 4 tissue damage parameters when evaluating the four parameters of tissue damage. The fourth parameter showed significant (p<0.05) differences in treatment results.

EXAMPLE 12—ALLERGIC CONJUNCTIVITIS

The safety and efficacy of IEP administered ophthalmically (topically) to patients demonstrating Allergic Conjunctivitis was evaluated in 6 patients. Subjects were randomly assigned to one of two methylcellulose based ophthalmic solutions containing 0.0% or 0.0067% IEP by weight. Treatment consisted of topical ophthalmic application of both ophthalmic solution concentrations to their randomly assigned patients 2 times a day for 5 days. There were no untoward effects seen by any patient. Each patient was clinically evaluated at 48 hours and 120 hours following the initiation of treatment for 2 parameters of tissue damage associated with Allergic Conjunctivitis. In addition, each patient was asked to evaluate subjectively 3 symptoms associated with Allergic Conjunctivitis 48 hours and 120 hours after treatment initiation. The percent reduction from the initial presentation of each of the parameters of tissue damage and the initial presentation for each additional symptom evaluated was calculated from 48 and 120 hour post treatment initiation data.

Prospective subjects were considered for the study only if their Allergic Conjunctivitis did not demonstrate an infectious element.

Patients were randomly assigned to one of two active levels being evaluated. This random assignment was made in groups of two patients to assure that each ophthalmic solution concentration was represented once in each group of two.

Clinical evaluation was performed at 48 hours and 120 hours post treatment initiation. Each patient was asked to subjectively evaluate 3 additional symptoms associated with Allergic Conjunctivitis by rating each symptom on a scale of 0 to 5 with 0 representing no evidence of symptom and 5 representing the greatest evidence of the symptom ever by the patient. Clinical evaluation of tissue damage parameters was also done using the same scale of 0 to 5.

Patient compliance with the treatment regimen and the use of other medications was also evaluated.

Tables 12.1, 12.2, 12.3, 12.4 and 12.5 list the identification letters assigned to each patient and the respective ophthalmic solution concentration. Tables 12.1, 12.2, 12.3, 12.4 and 12.5 also list the values for each patient prior to the beginning of treatment, at 48 hours and 120 hours post treatment initiation, for the treatment parameters Edema (Table 12.1) and Conjunctival Injection or redness (Table 12.2) as well as for the symptoms Itching (Table 12.3), Tearing (Table 12.4) and Level of Discomfort (Table 12.5).

TABLE 12.1

(Edema)

| Patient | Ophth Soln (%) | Value Prior to Treatment | Value at 48 Hours | Value at 120 Hours |
|---|---|---|---|---|
| A | 0.0067 | 3 | 1 | 0 |
| B | 0.0067 | 2 | 1 | 0 |
| C | 0.0067 | 1 | 0 | 0 |
| D | 0.0 | 3 | 4 | 3 |
| E | 0.0 | 2 | 3 | 3 |
| F | 0.0 | 3 | 2 | 2 |

TABLE 12.2

(Conjunctival Injection or Redness)

| Patient | Ophth Soln (%) | Value Prior to Treatment | Value at 48 Hours | Value at 120 Hours |
|---|---|---|---|---|
| A | 0.0067 | 3 | 1 | 0 |
| B | 0.0067 | 4 | 1 | 1 |
| C | 0.0067 | 2 | 3 | 4 |
| D | 0.0 | 2 | 3 | 4 |
| E | 0.0 | 2 | 2 | 1 |
| F | 0.0 | 4 | 3 | 3 |

TABLE 12.3

(Itching)

| Patient | Ophth Soln (%) | Value Prior to Treatment | Value at 48 Hours | Value at 120 Hours |
|---|---|---|---|---|
| A | 0.0067 | 4 | 0 | 0 |
| B | 0.0067 | 4 | 2 | 0 |
| C | 0.0067 | 3 | 0 | 0 |
| D | 0.0 | 3 | 3 | 3 |
| E | 0.0 | 2 | 3 | 1 |
| F | 0.0 | 4 | 3 | 3 |

TABLE 12.4

(Tearing)

| Patient | Ophth Soln (%) | Value Prior to Treatment | Value at 48 Hours | Value at 120 Hours |
|---|---|---|---|---|
| A | 0.0067 | 2 | 0 | 0 |
| B | 0.0067 | 4 | 2 | 1 |
| C | 0.0067 | 2 | 0 | 0 |
| D | 0.0 | 3 | 2 | 3 |
| E | 0.0 | 2 | 3 | 2 |
| F | 0.0 | 3 | 3 | 3 |

TABLE 12.5

(Level of Discomfort)

| Patient | Ophth Soln (%) | Value Prior to Treatment | Value at 48 Hours | Value at 120 Hours |
|---|---|---|---|---|
| A | 0.0067 | 3 | 1 | 1 |
| B | 0.0067 | 4 | 1 | 0 |
| C | 0.0067 | 2 | 0 | 0 |
| D | 0.0 | 3 | 3 | 3 |
| E | 0.0 | 3 | 3 | 2 |
| F | 0.0 | 4 | 3 | 3 |

From the data listed in Tables 12.1, 12.2, 12.3, 12.4 and 12.5, the percent reduction from the pre-treatment value for each parameter of tissue damage and each symptom was calculated for the 48 hour and the 120 hour values. These calculations are summarized in Table 12.6.

TABLE 12.6

(Percent Reduction from Pre-Treatment Value)

| Patient | Edema 48 hrs | Edema 120 hrs | Redness 48 hrs | Redness 120 hrs | Itching 48 hrs | Itching 120 hrs |
|---|---|---|---|---|---|---|
| A | 66.67 | 100.0 | 66.67 | 100.0 | 100.0 | 100.0 |
| B | 50.0 | 100.0 | 75.0 | 75.0 | 50.0 | 100.0 |
| C | 100.0 | 100.0 | 66.7 | 66.67 | 100.0 | 100.0 |
| D | [33.33] | 0.0 | [50.0] | [50.0] | 0.0 | 0.0 |
| E | [50.0] | [50.0] | 0.0 | 0.0 | [50.0] | 50.0 |
| F | 33.33 | 33.33 | 25.0 | 25.0 | 25.0 | 25.0 |

| Patient | Tearing 48 hrs | Tearing 120 hrs | Level of Discomfort 48 hrs | Level of Discomfort 120 hrs |
|---|---|---|---|---|
| A | 100.00 | 100.0 | 66.67 | 66.7 |
| B | 50.0 | 75.0 | 75.0 | 100.0 |
| C | 100.0 | 100.0 | 100.0 | 100.0 |
| D | 33.33 | 0.0 | 0.0 | 0.0 |
| E | [50.0] | 0.0 | 0.0 | 33.33 |
| F | 0.0 | 0.0 | 33.33 | 33.33 |

[ ] Represents a percent increase rather than reduction

In order to determine if these observed differences were significant, a statistical analysis of the percent reduction of each tissue damage parameter and each evaluated symptom associated with Allergic Conjunctivitis was performed. Both the 48 hour and 120 hour values from Table 12.6 for each tissue damage parameter and each symptom were subjected to an analysis of variance with treatment group (concentration) as a between-subject factor. The results of each of the omnibus tests for the 48 hour values are listed in Table 12.7. The results of each of the omnibus tests for the 120 hour values are listed in Table 12.8.

TABLE 12.7

(Analysis of Variance for Tissue Damage Parameters and Symptoms for 48 Hour Values from Table 12.6)

| Tissue Damage Parameter or Symptom | Calculated Value $F_{(2,4)}$ | Critical F Value $F_{(2,4)}$ | Significance Level (p<) |
|---|---|---|---|
| Edema | 9.15 | 6.94 | .05 |
| Redness | 12.25 | 6.94 | .05 |
| Itching | 11.00 | 6.94 | .05 |
| Tearing | 9.14 | 6.94 | .05 |
| Level of Discomfort | 21.56 | 18.00 | .01 |

TABLE 12.8

(Analysis of Variance for Tissue Damage Parameters and Symptoms for 120 Hour Values from Table 12.6)

| Tissue Damage Parameter or Symptom | Calculated Value $F_{(2,4)}$ | Critical F Value $F_{(2,4)}$ | Significance Level (p<) |
|---|---|---|---|
| Edema | 19.0 | 18.00 | .01 |
| Redness | 13.47 | 6.94 | .05 |
| Itching | 27.0 | 18.00 | .01 |
| Tearing | 121.0 | 18.00 | .01 |
| Level of Discomfort | 18.01 | 18.00 | .01 |

As can be seen from Tables 12.7 and 12.8, a significant (p<0.05) difference in treatment results occurred between the placebo ophthalmic solution and the ophthalmic solution containing active ingredient at 48 hours post treatment initiation for "edema", "redness", "itching", and for "tearing" and at 120 hours following the beginning of treatment for "redness". A highly significant (p<0.01) difference in treatment results occurred at the 120 hour post treatment initiation evaluations for the amount of "edema", "itching", and "tearing" seen. A highly significant (p<0.01) difference in treatment results occurred at both 48 hours and 120 hours post treatment for the "level of discomfort" felt by the patient.

The results of this study show that IEP demonstrated a greater percentage reduction in the tissue damage parameters and symptoms evaluated associated with Allergic Conjunctivitis. A statistical comparison between treatment results from the placebo ophthalmic solution and the ophthalmic solution containing active ingredient showed either significant (p<0.05) or highly significant (p<0.01) differences in treatment results when evaluating percent reduction from their original presentation level for parameters of tissue damage and symptoms associated with Allergic Conjunctivitis.

EXAMPLE 13—GIANT PAPILLARY CONJUNCTIVITIS

The safety and efficacy of IEP administered topically ophthalmically (topically) to patients demonstrating Giant Papillary Conjunctivitis was evaluated in 6 patients. Subjects were randomly assigned to one of two methylcellulose based ophthalmic solutions containing 0.0% or 0.0067% IEP by weight. Treatment consisted of topical ophthalmic application of both ophthalmic solution concentrations to their randomly assigned patients 2 times a day for 5 days. There were no untoward effects seen by any patient. Each patient was clinically evaluated at 48 hours and 120 hours following the initiation of treatment for 2 parameters of tissue damage associated with Giant Papillary Conjunctivitis. In addition, each patient was asked to evaluate subjectively 2 symptoms associated with Giant Papillary Conjunctivitis 48 hours and 120 hours after treatment initiation. The percent reduction from the initial presentation of each of the parameters of tissue damage and the initial presentation for each additional symptom evaluated was calculated from 48 and 120 hour post treatment initiation data.

Prospective subjects were considered for the study if their Giant Papillary Conjunctivitis did not demonstrate an infectious element.

Patients were randomly assigned to one of two active levels being evaluated. This random assignment was made in groups of two patients to assure that each ophthalmic solution concentration was represented once in each group of two.

Clinical evaluation was performed at 48 hours and 120 hours post treatment initiation. Each patient was asked to subjectively evaluate 2 additional symptoms associated with Giant Papillary Conjunctivitis by rating each symptom on a scale of 0 to 5 with 0 representing no evidence of symptom and 5 representing the greatest evidence of the symptom ever by the patient. Clinical evaluation of tissue damage parameters was also done using the same scale of 0 to 5. Patient compliance with the treatment regimen and the use of other medications was also evaluated.

Tables 13.1, 13.2, 13.3, and 13.4 list the identification letters assigned to each patient and the respective ophthalmic solution concentration. Tables 13.1, 13.2, 13.3 and 13.4 also list the values for each patient prior to the beginning of treatment, at 48 hours and 120 hours post treatment initiation, for the treatment parameters Conjunctival Injection or redness and Exudation as well as for the symptoms Itching and Burning and Contact Lens Tolerance.

TABLE 13.1

(Conjunctival Injection (redness))

| Patient | Ophth soln % | Value Prior to Treatment | Value at 48 hours | Value at 120 hours |
|---|---|---|---|---|
| A | 0.0067 | 4 | 2 | 0 |
| B | 0.0067 | 3 | 1 | 0 |
| C | 0.0067 | 2 | 0 | 0 |
| D | 0.0 | 4 | 3 | 4 |
| E | 0.0 | 2 | 2 | 2 |
| F | 0.0 | 1 | 2 | 2 |

TABLE 13.2

(Exudation)

| Patient | Ophth soln % | Value Prior to Treatment | Value at 48 hours | Value at 120 hours |
|---|---|---|---|---|
| A | 0.0067 | 4 | 2 | 0 |
| B | 0.0067 | 4 | 1 | 0 |
| C | 0.0067 | 2 | 0 | 0 |
| D | 0.0 | 3 | 4 | 5 |
| E | 0.0 | 2 | 2 | 3 |
| F | 0.0 | 2 | 2 | 2 |

TABLE 13.3

(Itching and Burning)

| Patient | Ophth soln % | Value Prior to Treatment | Value at 48 hours | Value at 120 hours |
|---|---|---|---|---|
| A | 0.0067 | 4 | 1 | 0 |
| B | 0.0067 | 5 | 1 | 0 |
| C | 0.0067 | 3 | 0 | 0 |
| D | 0.0 | 4 | 4 | 4 |
| E | 0.0 | 2 | 3 | 4 |
| F | 0.0 | 3 | 2 | 3 |

TABLE 13.4

(Contact Lens Tolerance)

| Patient | Ophth soln % | Value Prior to Treatment | Value at 48 hours | Value at 120 hours |
|---|---|---|---|---|
| A | 0.0067 | 4 | 1 | 0 |
| B | 0.0067 | 1 | 1 | 0 |
| C | 0.0067 | 3 | 0 | 0 |
| D | 0.0 | 5 | 4 | 4 |
| E | 0.0 | 2 | 3 | 4 |
| F | 0.0 | 3 | 3 | 3 |

From the data listed in Tables 13.1, 13.2, 13.3, and 13.4, the percent reduction from the pre-treatment value for each parameter of tissue damage and each symptom was calculated for the 48 hour and the 120 hour values. These calculations are summarized in Table 13.5 on the next page.

TABLE 13.5

(Percent Reduction from Pre-Treatment Value)

| Patient | Redness | | Exudation | |
|---|---|---|---|---|
| | 48 hr | 120 hr | 48 hr | 120 hr |
| A | 50.0 | 100.0 | 50.0 | 100.0 |
| B | 66.67 | 100.0 | 75.0 | 100.0 |
| C | 100.0 | 100.0 | 100.0 | 100.0 |
| D | 25.0 | 0.0 | [33.33] | [66.67] |
| E | 0.0 | 0.0 | 0.0 | [33.33] |
| F | [100.0] | [100.0] | 0.0 | 0.0 |

| Patient | Itch/Burn | | Contact Lens Tolerance | |
|---|---|---|---|---|
| | 48 hr | 120 hr | 48 hr | 120 hr |
| A | 75.0 | 100.0 | 75.0 | 100.0 |
| B | 80.0 | 100.0 | 0.0 | 100.0 |
| C | 100.0 | 100.0 | 100.0 | 100.0 |
| D | 0.0 | 0.0 | 20.0 | 20.0 |
| E | [50.0] | [100.0] | [50.0] | [100.0] |
| F | 33.33 | 0.0 | 0.0 | 33.33 |

[ ] Represents a percent increase rather than reduction

It should be noted that a significant decrease in size of the papilla was not noted for any of the patients in this study by the end of the 5 day treatment period.

In order to determine if these observed differences were significant, a statistical analysis of the percent reduction of each tissue damage parameter and each evaluated symptom associated with Giant Papillary Conjunctivitis was performed. Both the 48 hour and 120 hour values from Table 13.5 for each tissue damage parameter and each symptom were subjected to an analysis of variance with treatment group (concentration) as a between-subject factor. The results of each of the omnibus tests for the 48 hour values are listed in Table 13.6. The results of each of the omnibus tests for the 120 hour values are listed in Table 13.7.

TABLE 13.6

(Analysis of Variance for Tissue Damage Parameters and Symptoms for 48 Hour Values from Table 13.5)

| Tissue Damage Parameter or Symptom | Calculated Value $F_{(2,4)}$ | Critical F Value $F_{(2,4)}$ | Significance Level ($p<$) |
|---|---|---|---|
| Redness | 8.19 | 6.94 | .05 |
| Exudation | 22.35 | 18.00 | .01 |
| Itching/Burning | 12.72 | 6.94 | .05 |
| Contact Lens Tol. | 3.49 | 6.94 | — |

TABLE 13.7

(Analysis of Variance for Tissue Damage Parameters and Symptoms for 120 Hour Values from Table 13.5)

| Tissue Damage Parameter or Symptom | Calculated Value $F_{(2,4)}$ | Critical F Value $F_{(2,4)}$ | Significance Level ($p<$) |
|---|---|---|---|
| Redness | 16.0 | 6.94 | .05 |
| Exudation | 48.01 | 18.00 | .01 |
| Itching/Burning | 16.0 | 6.94 | .05 |
| Contact Lens Tol. | 7.43 | 6.94 | .05 |

As can be seen from Tables 13.6 and 13.7, a significant ($p<0.05$) difference in treatment results occurred between the placebo ophthalmic solution and the ophthalmic solution containing active ingredient both at 48 hours and at 120 hours post treatment initiation for "redness" and "itching and burning" and for "contact lens tolerance" at 120 hours following the beginning of treatment. A highly significant ($p<0.01$) difference in treatment results occurred at the 48 and 120 hour post treatment initiation evaluations for the amount of "exudation" seen.

The results of this study show that IEP demonstrated a greater percentage reduction in the tissue damage parameters and symptoms evaluated associated with Giant Papillary Conjunctivitis. A statistical comparison between treatment results from the placebo ophthalmic solution and the ophthalmic solution containing active ingredient showed either significant ($p<0.05$) or highly significant ($p<0.01$) differences in treatment results when evaluating percent reduction from their original presentation level for parameters of tissue damage and symptoms associated with Giant Papillary Conjunctivitis (with the exception of contact lens tolerance at 48 hours post treatment initiation.

DISCUSSION OF EXAMPLES

As the above observations indicate, the preparation as described is effective in treating numerous topical lesions inflammations, or lesions resulting from compromise or reaction of the immune system.

Concentrations of IEP from approximately 0.00325 percent to 0.0275 percent, represent dosage levels far less than the dosage levels when IEP has been given systemically in the prior art, and from 6 to 50 times less than when given intradermally in the prior art. Since IEP is largely inactivated when ingested, no adverse effects are anticipated from topical applications. Based on the pharmacology of IEP, we suspect that substantial further increases in the concentration of IEP may lead to adverse topical reactions in some patients.

It is not understood why the excellent results described above have been achieved. However, the inventors recognize that there are similarities in the chemical structure of histamine and histone. Histone is a naturally occurring body substance that takes the form of a thin protein coat on genetic material. If the histone coat is damaged, for example by a virus, physical injury, or other factor, the damage may alter the properties of the histone coating enough that the genetic messages produced by the cell to reproduce itself or genetic messages of the cell acted upon by the human immune system are misinterpreted by the cell or by the immune system.

Although not wanting the invention to be limited by any particular theory or mechanism, the inventors believe that providing histamine locally to the area of the damage, rather than providing histamine systemically, may provide "building blocks" that result in natural regeneration of the histone coat on the cell and avoid misinterpretation of the cell's chemical messages, thereby avoiding undesirable responses by the immune system, or avoiding tumorous or cancerous cell growth. Perhaps the histamine acts at the genetic level in the vicinity of the histone coat, and performs one or more of the following functions:

(1) providing building blocks to repair the histone coat;
(2) providing stimulation of the genetic material, e.g., the basic chromosome within the cell, to react to trauma or damage of the cell to cause tissue repair; or
(3) reacting in such a way as to prevent a virus or the like from utilizing the genetic material within the cell to duplicate itself. (It should be appreciated that it is desirable to avoid systemic doses of histamine in the human body, because excessively high levels of histamine can cause a variety of problems and systems, some of which are specific to the gastrointestinal tract, and others of which can cause allergic reactions ranging from minor rashes to anaphylactic shock. Those skilled in the art certainly know that it would be undesirable to provide systemic treatments for localized lesions.)

It is also possible that during viral replication the viral genome incorporates a nucelotide (or nucleotides) which contain histamine, or some variation thereof, which in turn renders the viral genome non-functional and/or unable to replicate.

We think that histamine phosphate, carried by the CARBOPOL, may be creating a negative feedback response or mechanism to prevent further histamine release that usually occurs in inflammatory processes from mast cells in which histamine is usually stored in the body. This mechanism has been referred to as mast cell stabilizing and the product causing it is known as a mast cell stabilizer. The mast cells recognize histamine already present and therefore do not respond by releasing histamine that is stored within them, in effect providing a negative feedback response.

While the invention has been described with reference to a number of particular embodiments thereof, those skilled in the art will be able to make various modifications to the described embodiment without departing from the true spirit and scope of the invention. It should be appreciated that so-called "precursor IEP" substances or "prodrug" substances which are used in production of drugs might be useable in place of IEP. Such a prodrug may not itself be active, but may be modified by the body into an active drug that results in IEP locally.

What is claimed is:

1. A method of making a formulation for topical treatment of herpes labialis, herpes genitalis, herpes zoster, varicella zoster, aphthous stomatitis, oral mucositis secondary to chemotherapy, photodermatitis, thermal burns, and decubitus ulcers, comprising the steps of adding vinyl polymer to distilled water, allowing the resulting mixture to stand until the vinyl polymer mixture is wetted, blending the mixture with a high speed blender until a homogenous mixture is formed, adding a dispersing agent to form an emulsion, adding 0.00325 percent to 0.0275 percent 1H-imidazole-4-ethanamine, phosphate by weight to the emulsion and mixing it until the resulting mixture is homogenous.

2. A composition for topical treatment of epithelial lesions including the skin, mucous membranes of the oral cavity, genitalia, vagina, and conjunctiva, consisting essentially of water soluble vinyl polymer gel uniformly mixed with approximately 0.00325 to 0.0275 percent by weight 1H-imidazole-4-ethanamine, phosphate.

3. A composition for topical treatment of epithelial lesions including herpes labialis, herpes genitalis, herpes zoster, varicella zoster, aphthous stomatitis, oral mucositis secondary to chemotherapy, photodermatitis, thermal bums, and decubitus ulcers, consisting essentially of a water soluble vinyl polymer gel uniformly mixed with approximately 0.00325 to 0.0275 percent by weight 1H-imidazole-4-ethanamine, phosphate.

4. A method of treating epithelial lesions including lesions of the skin, mucous membranes of the oral cavity, genitalia, vagina and conjunctiva, comprising topically applying a composition comprising a water soluble vinyl polymer gel or ophthalmic solution comprising approximately 0.00325 to 0.0272 percent by weight 1H-imidazole-4-ethanamine, phosphate uniformly mixed therewith to the lesions.

5. A method of treating herpes lesions comprising topically applying a composition comprising a water soluble vinyl polymer gel comprising approximately 0.0067 to 0.0275 percent by weight 1H-imidazole-4-ethanamine, phosphate uniformly mixed therewith to the lesions.

6. A method of treating inflammatory reactions or lesions of the epithelium including inflammation and lesions of the skin, mucous membranes of the oral cavity, genitalia, vagina and conjunctiva, comprising topically applying a composition comprising a water soluble vinyl polymer gel, lotion or ophthalmic solution comprising approximately 0.00325 to 0.0275 percent by weight 1H-imidazole-4-ethanamine, phosphate uniformly combined therewith to the inflammatory reaction or lesion.

7. A method of treating lesions of the epithelium including lesions of the skin, mucous membranes of the oral cavity, genitalia, vagina and conjunctiva, which result from conditions of compromise or reaction by the immune system, comprising topically applying a composition comprising a water soluble vinyl polymer gel, lotion, or ophthalmic solution comprising approximately 0.00325 to 0.0275 percent by weight 1H-imidazole-4-ethanamine, phosphate uniformly combined therewith to the lesion resulting from conditions of compromise or reaction of the immune system.

* * * * *